(12) United States Patent
Zebala et al.

(10) Patent No.: US 8,129,383 B2
(45) Date of Patent: *Mar. 6, 2012

(54) AMINOPTERIN DOSAGE FORMS AND METHODS FOR INFLAMMATORY DISORDERS

(75) Inventors: John Zebala, Sammamish, WA (US); Barton A. Kamen, Princeton Junction, NJ (US)

(73) Assignee: Aminopterin LLC, Auburn, WA (US)

( * ) Notice: Subject to any disclaimer, the term of this patent is extended or adjusted under 35 U.S.C. 154(b) by 618 days.

This patent is subject to a terminal disclaimer.

(21) Appl. No.: 11/928,890

(22) Filed: Oct. 30, 2007

(65) Prior Publication Data

US 2008/0108621 A1 May 8, 2008

Related U.S. Application Data

(63) Continuation-in-part of application No. 11/078,271, filed on Mar. 11, 2005, now Pat. No. 7,312,217.

(51) Int. Cl.
*A61K 31/505* (2006.01)
(52) U.S. Cl. ........ 514/249; 514/825; 514/863; 514/886; 514/903
(58) Field of Classification Search .................... 514/249
See application file for complete search history.

(56) References Cited

U.S. PATENT DOCUMENTS 6,673,908 B1 * 1/2004 Stanton, Jr.

OTHER PUBLICATIONS

Collins English Dictionary. London: Collins, 2000. s.v. "cycle," http://www.credoreference.com/entry/hcengdict/cycle (accessed Feb. 25, 2010).*
Olivry et al., Veterinary Immunology and Immunopathology, 2001, vol. 81, pp. 317-322.*
Anderson, et al., Eur. J. Pharm. Sci. 9(4):333-43, 2000.
Galivan, et al., Methotrexate in adjuvant arthritis, in Chemistry and Biology of Pteridines 1986. Pteridines and Folic Acid Derivatives, B.A. Cooper & V.M. Whitehead, Editors.
Edmundson and Guy, Ama Arch. Derm. 78(2):200-3, Aug. 1958.
Gubner, A.M.A. Arch. Derm. and Syphil. Chicago 64:688, 1951.
Gubner et al., Am. J. Med. Sci. 22:176, 1951.
Gubner et al., J. Invest. Dermatol. 19(4):297-305, Oct. 1952.
Page, Ann. N.Y. Acad. Sci. 116:950-63, Aug. 27, 1964.
Rees et al., AMA Arch. Derm. 72(2):133-43, Aug. 1955.
Rees et al., Arch. Dermatol. 90:544-52, Dec. 1964.
Rees et al., Arch. Dermatol. 83:970-72, Jun. 1961.
Rees and Bennett, J. Invest. Dermatol. 32(1):61-66, Jan. 1959.
Strakosch, Dermatologica. 126:259-267, 1963.
Ratliff, et al., J. Clin. Oncol. 16(4):1458-1464. 1998.
Ben-Gurion, R. Nature. 4859:1121. Dec. 15, 1962.
Olivry et al., "A pilot open trial evaluating the efficacy of low-dose aminopterin in the canine homologue of atopic dermatitis" Brit. J. Dermatology 157:1040, 2007.

* cited by examiner

*Primary Examiner* — James D Anderson
*Assistant Examiner* — Gregg Polansky
(74) *Attorney, Agent, or Firm* — Jeffrey B. Oster

(57) ABSTRACT

There is disclosed dosage forms and methods for treating a patient with an inflammatory disorder with a therapeutically effective amount of aminopterin, or a pharmaceutically acceptable salt thereof, that achieve efficacy without concomitant toxicity. Specifically, there is disclosed a method for treating an inflammatory disorder in a patient with uninterrupted doses of aminopterin.

11 Claims, 6 Drawing Sheets

Squares = mean percent reduction in CADESI score; Diamonds = mean reduction in pruritis score.

AMINOPTERIN DOSAGE FORMS AND METHODS FOR INFLAMMATORY DISORDERS

This is a continuation-in-part of pending application Ser. No. 11/078,271, filed 11 Mar. 2005.

BACKGROUND

Aminopterin, or 4-amino-pteroyl-L-glutamic acid, is a potent antifolate [see Franklin, U.S. Pat. No. 2,575,168]. Aminopterin binds and inhibits dihydrofolate reductase (DHFR) from a variety of species, including humans. Synthesized in 1946 by the Lederle Laboratories, a division of American Cyanamid Co., aminopterin was marketed in 0.5 mg tablets in 1953 for the treatment of childhood leukemia. In 1965, the marketing of aminopterin as a pharmaceutical in the United States ceased.

In 1951, Gubner treated patients with rheumatoid arthritis, psoriatic arthritis, uncomplicated psoriasis, and atopic dermatitis with 0.75-2 mg/day for durations of approximately 1 week and greater, or cumulative weekly doses of greater than 5.25 mg [Gubner et al., *Am J. Med. Sci.* 22:176, 1951; and Gubner, *Arch. Derm.*, Chicago 64:688, 1951]. Although some patients improved, the majority of patients developed toxic reactions including stomatitis, nausea, diarrhea, and alopecia that necessitated discontinuation of the drug. Gubner concluded that "the toxic effects of aminopterin place practical limitations on its use as a therapeutic agent" [Gubner et al., *Am. J. Med. Sci.* 22:176, 1951].

In 1955, Rees et al. treated 171 patients with psoriasis with five dosage schedules using the 0.5 mg tablet that comprised: (i) 1 tablet daily for six days; (ii) 1 tablet daily for six days, one week rest, then 1 tablet daily for six days; (iii) 1 tablet daily for 12 days; (iv) 2 tablets daily for six days; and (v) 2 tablets daily for three days, then 1 tablet daily for six days [Rees et al., *AMA Arch. Derm.* 72(2):133-43, August 1955]. A rapid clearing of psoriatic lesions were noted, with toxic reactions occurring with a frequency of 0%, 2.5%, 13%, and 30% on schedules (i), (ii), (iii) and (iv), respectively. Too few patients were treated with schedule (v) to assess. Toxic reactions included stomatitis, alopecia, and leucopenia. When the above schedules were concluded, the psoriatic lesions invariably recurred, usually within weeks. Some patients were given multiple courses of the above schedules, with rest periods between courses.

In 1958, Edmundson and Guy treated patients with a schedule comprising 1 tablet daily for six days, withdrawal for three days, and again daily for six days, for a total of 6 mg in 12 doses [Edmundson and Guy, *AMA Arch. Derm.* 78(2): 200-3, August 1958]. Improvement was noted, and remissions typically lasted several months.

In 1959, Rees and Bennett report the treatment of 329 patients with psoriasis using the same schedules from their 1955 study [Rees and Bennett, *J. Invest. Dermatol.* 32(1):61-66, January 1959). Courses of the schedules were repeated in some patients every 3 weeks to once every 3 years, although it is not disclosed which schedules were repeated. The overall incidence of toxicity was 21% and the most common toxic reactions were stomatitis and intensification of the lesions, followed by alopecia, GI disturbances, and leucopenia. The authors noted that treatment should be discontinued at the slightest hint of a toxic reaction.

In 1961, Rees and Bennett compared the effect of daily doses of 0.5 mg aminopterin against daily doses of 2.5 mg methotrexate using the same schedules from their 1955 study [Rees and Bennett, *Arch. Dermatol.* 83:970-72, June 1961].

In 1963, Strakosh also compared the effect of daily doses of 0.5 mg aminopterin against daily doses of 2.5 mg methotrexate according to schedules comprising: (i) 1 tablet daily for 12 days, followed by one-week's rest, and repeated as often as deemed advisable; (ii) 1 tablet daily for 3 days followed by three-days' rest period and repeated until 12 tablets in all were given, and then followed by one-week's rest period and repeated as often as deemed advisable (i.e., four cycles interrupted by a week rest each); and (iii) any variation of (i) and (ii) above [Strakosch, *Dermatologica* 126:259-267, 1963]. Both concluded that methotrexate is less toxic and less efficacious than aminopterin in treating psoriasis. However, the doses compared were not equipotent to one another, with methotrexate being used in an amount 4-fold less than would be required to be equipotent with aminopterin. Thus, by modern standards no conclusions could be drawn regarding the actual relative efficacy, toxicity, or therapeutic index of these antifolates. Later, Rees et al. suggest the opposite, that methotrexate may be more safe and efficacious than aminopterin in treating psoriasis [Rees et al., *Arch. Dermatol.* 90:544-52, December 1964].

In 1964, Rees et al. review the literature on the standard of practice with aminopterin in treating psoriasis, describing all known schedules of administration [Rees et al., *Arch. Dermatol.* 90:544-52, December 1964]. In all cases, dosing schedules were similar, being comprised of daily dosings of tablets for periods greater than 1 week until efficacy or toxicity was observed, at which time dosing was interrupted by rest periods of varying duration.

The prior art are also contains several reports of using aminopterin to reduce inflammation in animal models. In 1952, Gubner et al. demonstrated the efficacy of cumulative weekly doses of 0.3 mg/kg aminopterin in the rat formaldehyde arthritis model [Gubner et al., *J. Invest. Dermatol.* 19(4): 297-305, October 1952]. In 1964, Page demonstrated the efficacy of cumulative weekly doses of 0.35 mg/kg aminopterin in the rabbit dermal inflammation model, but in the process the animals became severely leucopenic and one subject died [Page, *Ann. N.Y. Acad. Sci.* 116:950-63, Aug. 27, 1964]. In 1986, Galivan et al. demonstrated the efficacy of cumulative weekly doses of 0.12 mg/kg aminopterin in the rat adjuvant arthritis model, but the animals suffered from severe toxicity [Galivan, et al., Methotrexate in adjuvant arthritis, in *Chemistry and Biology of Pteridines* 1986. *Pteridines and Folic Acid Derivatives*, B. A. Cooper and V. M. Whitehead, Editors. 1986, Walter de Gruyter & Co.: Berlin. p. 847-49]. Similarly, in 2000 Andersson et al. demonstrated the efficacy of cumulative weekly doses of >1.5 mg/kg aminopterin in the rat antigen-induced arthritis model, but again the animals suffered from severe toxicity [Andersson, et al., *Eur. J. Pharm. Sci.* 9(4):333-43, 2000].

Inflammatory diseases, whether of a chronic or acute nature, represent a substantial problem in the healthcare industry. Chronic inflammation is considered to be inflammation of a prolonged duration (weeks or months) in which active inflammation, tissue destruction and attempts at healing are proceeding simultaneously (Cotran, R. S., Kumar, V., and Robbins, S. L., Robbins Pathological Basis of Disease. W.B. Saunders Co., p. 75, 1989). Although chronic inflammation can follow an acute inflammatory episode, it can also begin as an insidious process that progresses with time, for example, as a result of a persistant infection (e.g., tuberculosis, syphilis, fungal infection) which causes a delayed hypersensitivity reaction, prolonged exposure to endogenous (e.g., elevated plasma lipids) or exogenous (e.g., silica, asbestos, cigarette tar, surgical sutures) toxins, or autoimmune reactions against the body's own tissues (e.g., rheumatoid arthritis, systemic lupus erythematosus, multiple sclerosis, psoriasis). Chronic inflammatory diseases include many common medical conditions such as rheumatoid arthritis, restenosis, psoriasis, multiple sclerosis, surgical adhesions, tuberculosis, chronic inflammatory lung diseases (e.g. asthma, pneumoconiosis, chronic obstructive pulmonary disease, nasal polyps and pulmonary fibrosis), periodontal disease (i.e. periodontitis) and polycystic kidney disease.

Multiple sclerosis (MS), affecting 350,000 people (women:men=2:1) in the United States with 8,000 new cases reported each year, is the most common chronic inflammatory disease involving the nervous system. The predominant pathologic findings are demyelination accompanied by disruption of underlying axons (Trapp et al., *New Engl. J. Med.* 338:278-85, 1998; Prineas, J. W., "Pathology of Multiple Sclerosis" in: Cook, S. D., ed. Handbook of Multiple Sclerosis. New York: Marcel Dekker, Inc., 1990:187-215). The disease affects young adults who usually present with a relapsing, remitting pattern of neurologic involvement and progress to a chronic phase with increasing difficulty in ambulation and coordination. Roughly half of MS cases progress to a more chronic phase. Although the disease does not result in early death or impairment of cognitive functions, it cripples the patient by disturbing visual acuity; simulating double vision; disturbing motor functions affecting walking and use of the hands; producing bowel and bladder incontinence; spasticity; and sensory deficits (touch, pain and temperature sensitivity).

MS is a demyelinating disease of the CNS with unknown cause and no known cure. Though single episodes of demyelination can occur, once the disease is established in multiple sites in the brain, spinal cord, and optic nerves, MS frequently follows a clinically relapsing-remitting course while lesions in the CNS continue to progress. During this phase, an immune mediated inflammatory response to myelin antigens is thought to play a major role in the pathogenesis of developing lesions. Then, in a clinically progressive phase, at least fifty-five percent of patients worsen, with clinical relapses sometimes punctuating their clinical decline. The mechanism of tissue damage to the CNS is not known with certainty in the progressive phase of MS. It is thought, however, that axonal damage, perhaps through some type of immune mediation, is important in this phase of the disease, though some axonal damage certainly occurs during the inflammatory phase. Perivascular infiltration of T lymphocytes and macrophages in brain lesions is one of the characteristics of MS. Activation of myelin-reactive T cells in the periphery is an early event in the MS process. These activated T cells facilitate the production of B cells of antibodies against myelin, and activate macrophages to attack oligodendrocytes in the CNS. Treatment options for patients with MS are limited. Currently, the primary drugs used to treat MS are interferons and glatiramer acetate. Such treatments have been shown to slow, but not arrest, the clinical course of progression in progressive MS.

Experimental Autoimmune Encephlomyelitis (EAS) is an experimental model for human MS (Mackay, et al., *Clin. Exp. Immunol.* (1973) 15:471-82). The use of this model can be demonstrated in guinea pigs (Lisak, et al., *J. Immunol.* (1970) 104(6):1435-47); hens (Blaszczyk, et al., *Folia biologica* (Praha) (1977) 23:299; female rats (Levine, and Sowinski, *Arch. Int. Pharmacodyn.* (1977) 230:309-318; Badger, et al., *Agents and Actions* (1989) 27 (3/4):335-7; Desai, and Burton, *Agents and Actions* (1989) 27 (3/4): 351-355; Vogel, et al., *Can. Res.* (1969) 29:2249-2253; Przuntek, et al., *Neuropharma.* (1987) 26(2/3):255-260); male rats (Rosenthale, et al., *Arch Int. Pharmacodyn.* (1969) 179(2):251-275); rabbits (Brandiss, et al., *Ann. NY Acad. Sci.* 356-368); and male and female rats (Levy, and Whitehouse, *Agents and Actions* (1974) (4/2):113-116; Martel, et al., *Can. J. Physiol. Pharmacol.* (1977) 55:48-51).

Chronic inflammatory lung disease, including for example, asthma, pneumoconiosis, chronic obstructive pulmonary disease, nasal polyps, and pulmonary fibrosis, affect many people worldwide. Typically such diseases are characterized by an invasive inflammatory process, and thickening of the affected tissues.

Asthma is an inflammatory disease that is associated with widespread but variable airflow obstruction. Asthma is defined as a "disease characterized by an increased responsiveness of the trachea and bronchi to various stimuli, and manifested by widespread narrowing of the airways that changes in severity either spontaneously or as a result of treatment" (American Thoracic Society). About 5% of the population suffers from asthma. The pathogenesis of asthma is poorly understood. Multiple complex immune system mechanisms probably are involved. Numerous cytokines derived from tissue mast cells, eosinophils, T lymphocytes, macrophages, neutrophils, and other lung cells are critical in initiating and perpetuating the asthmatic response and play important roles in the immunopathogenesis of airways in inflammation (Current Medical Diagnosis & Treatment, $36^{th}$ ed.). In persons with asthma, the airways narrow (bronchoconstriction) in response to stimuli that don't affect the airways of normal lungs. The narrowing can be triggered by many stimuli (an allergen), such as pollens, dust mites, animal dander, smoke, cold air, and exercise. Bronchodilator drugs that relieve attacks of asthma through non-specific blockade of beta-adrenergenic receptors cause side effects such as rapid heartbeat, restlessness, headache, and muscle tremors. Theophylline is another bronchodilator drug whose administeration must be closely monitored by a doctor, because too little drug in the blood may give little benefit, and too much drug may cause life-threatening abnormal heart rhythms or seizures and patients may also experience insomnia, agitation, and vomiting. Corticosteriods drugs are exceptionally effective at reducing asthma symptoms by blocking the body's inflammatory response but long term use may result in poor wound healing, loss of calcium from the bones, stomach bleeding, premature cataracts, elevated blood sugar levels, hunger, weight gain, mental problems, and stunted growth in children.

The benefits of asthma treatments have been investigated in animals (Nagao, et al., *J. Pharma. Pharmacol.* (2004), 56:187-196) and humans (Comet, et al., *Resp. Med.* (2006), 100:411-19; Rabe, et al., *Lancet.* 368:744-53; Busse, et al., *Ann. All. Asth. Immunol.* 96:60-68; Johnston, et al., *New Engl. J. Med.* 354 (15):1589-1600; Bateman, et al., *Ann. All. Asth. Immunol* 96:679-686).

Systemic lupus erythematosus (SLE) is a disorder of the immune system. Lupus can affect many parts of the body, including the joints, skin, kidneys, heart, lungs, blood vessels and brain. Although patients with the disease may have many different symptoms, some of the most common ones include extreme fatigue, painful or swollen joints (arthritis), unexplained fever, skin rashes, and kidney problems. Other symptoms include chest pain upon deep breathing, unusual loss of hair, pale or purple fingers from cold or stress (Raynaud's phenomenon), sensitivity to sun, swelling (edema) in legs or around eyes, mouth ulcers and swollen glands. New symptoms may continue to appear years after the initial diagnosis, and different symptoms can occur at different times. Several systems of the body may be affected including the kidneys, lungs, CNS, blood vessels, blood and heart.

Several methods of treatment are currently employed to treat SLE. Nonsteroidal anti-inflammatory drugs (NSAIDS) are often used, either alone or in combination, including ibuprofen and naproxen. Common side effects include stomach upset, heartburn, diarrhea and fluid retention. Antimalarials, such as hydrochloroquinone, are also commonly used to treat lupus. They are generally used to treat fatigue, joint pain, skin rashes, and inflammation of the lungs. Side effects include stomach upset, and, rarely, damage to the retina of the eye. Corticosteroids are also used to treat lupus. Examples include prednisone, hydrocortisone, methylprednisone and dexamethasone. Short-term side effects include swelling, increased appetite and weight gain. These side effects generally stop when the drug is stopped. Long-term side effects can include stretch marks of the skin, weakened or damaged bones (osteoporosis and osteonecrosis), high blood pressure, damage to the arteries, diabetes, infections and cataracts. Typically, the higher the dose and the longer they are taken, the greater the risk and severity of side effects. For some patients whose kidneys or CNS are affected by lupus, immunosuppressives may be used. These include cyclophosamide and mycophenolate mofetil. Side effects may include nausea, vomiting, hair loss, bladder problems, decreased fertility, and increased risk of cancer and infection. The risk for side effects increases with the length of treatment.

Polymyositis is a disease of muscle featuring inflammation of the muscle fibers. The muscles typically affected are those closest to the trunk or torso. Polymyositis can be associated with skin rash and is then referred to as dermatomyositis. It also can affect other areas of the body. Weakness of muscles is the most common symptom of polymyositis. The onset can be gradual or rapid. This results in varying degrees of loss of muscle power and atrophy. Patients can also feel fatigue, a general feeling of discomfort and have weight loss and/or low grade fever. Heart and lung involvement can lead to irregular heart rhythm, heart failure, and shortness of breath. Initially, polymyositis is treated with high doses of corticosteroids and are usually required for years. Corticosteroids have many predictable and unpredictable side effects. In high doses they commonly cause increase in appetite and weight, puffiness of the face and easy bruising, sweats, facial hair growth, upset stomach, sensitive emotions, leg swelling, acne, cataracts, osteoporosis, high blood pressure, worsening of diabetes, increased risk of infection, and rarely, avascular necrosis. Further, abruptly stopping corticosteroids can cause flares of the disease and result in other side effects including nausea, vomiting and decreased blood pressure. Immunosupressives may used in the cases where corticosteroids do not adequately improve polymyositis. These include the use of methotrexate and azathioprine. These medications can cause liver and bone marrow side effects and require blood monitoring. Cyclophosphamide, chlorambucil and cyclosporine may also be used, however these compounds also have serious side-effects.

Graft-versus-host-disease (GVHD), an immune effect, is the most common complication among patients who survive beyond 100 days after allogenic hematopoietic cell transplantation. The incidences of acute GVHD (aGVHD) and chronic GVHD (cGVHD) are 30-80% and 30-80%, respectively. GVHD itself and treatment-related infections are the principal causes of nonrelapse mortality. For aGVHD after methotrexate alone or methotrexate in combination with cyclosporine A as prophylaxis regimens, methylprednisone is the best initial therapy. Prednisone and cyclosporine A are considered as the first-line therapy for patients with cGVHD. Other therapeutic options for aGVHD or cGVHD are anti-thymocyte globulin, mycophenolate mofetil, tacrolimus, azathioprine, thalidomide, monoclonal antibodies directly against CD3, CD25, CD52, cytotoxic T-lymphocyte antigen (CTLA)-4 or tumor necrosis factor alpha, extracorporeal photochemotherapy and PUVA therapy. Most immunosuppressive agents require continuous administration of the drug to be effective. Consequently, infectious complications are frequently observed and tremendously increase the treatment cost. Although treatment with cyclosporine and gluccocorticoids can control manifestations of cGVHD in some patients, the therapeutic options are limited for those with steroid-refractory cGVHD.

SUMMARY

The present disclosure provides dosages and methods for treating a patient with an inflammatory disorder with a therapeutically effective amount of aminopterin, or a pharmaceutically acceptable salt thereof. The present disclosure provides unexpected advantages of patient convenience without creating concomitant toxicity manifestations. In particular, it has been discovered that aminopterin can be used in uninterrupted cycles of doses as an anti-inflammatory agent, and in some embodiments at doses lower than previously taught in the art.

There is disclosed a method for treating inflammatory conditions with aminopterin without creating unacceptable toxicity manifestations. Another related embodiment is a method of treating bronchopulmonary dysplasia, canine atopic dermatitis, and bovine acute pneumonic pasteurellosis with an antifolate, and aminopterin in particular. Another related embodiment is a method of treating inflammatory bowel disease, asthma, and multiple sclerosis (MS) with aminopterin. Another related embodiment is a method of treating systemic lupus erythematosus (SLE), graft-versus-host-disease (GVHD) and polymyositis with aminopterin. Further, it has been discovered that aminopterin doses can be administered in dosage forms containing less aminopterin per tablet than described by earlier publications. These lower doses are achieved by the development of tablets containing less than 0.5 mg aminopterin, which allow lower doses to be administered to patients and also allow the ability to tailor these lower doses more accurately to a particular patient's body weight.

Another aspect is treatment of rheumatoid arthritis, psoriatic arthritis and atopic dermatitis in humans with a weekly dose of aminopterin of 5.25 mg or less. A related embodiment is a method of dosing a human with psoriasis with a cumulative weekly dose of less than 2 mg aminopterin. A related embodiment is a dosage form of aminopterin containing less than 0.5 mg per tablet. It will be appreciated by one in the art that the above identified aspects avoid the toxicity and irregular dosing schedules of aminopterin that were a major inconvenience to patients with inflammatory disorders. Another aspect of the disclosure are tablets containing less than 0.5 mg aminopterin per tablet, which make it possible to administer lower doses and also make it easier to tailor lower doses to a particular patient's weight in order to avoid toxicity.

Another aspect of the disclosure is treatment of MS, polymyositis, SLE, GVHD or asthma in humans with a weekly dose of aminopterin of 7.5 mg/week or less. A related embodiment is a method of dosing a human with MS or asthma with a cumulative weekly dose of less than 5.25 mg or less of aminopterin. A related embodiment is a method of dosing a human with MS, polymyositis, SLE, GVHD or asthma with a cumulative weekly dose of less than 2 mg aminopterin. Another related embodiment is a method of dosing a human with MS, polymyositis, SLE, GVHD or asthma with a cumulative weekly dose of less than 1 mg/kg aminopterin.

Further still, antifolates and aminopterin in particular have been discovered to be efficacious in the treatment of bronchopulmonary dysplasia, and inflammatory disorders that occur naturally in domestic and agricultural animals, and in some embodiments with only a single dose of aminopterin. In particular, embodiments provide:

A method for treating an inflammatory disorder in a patient, comprising administering to said patient a therapeutically effective amount of aminopterin, or a pharmaceutically acceptable salt thereof, in uninterrupted cycles. In preferred embodiments, the number of uninterrupted cycles is at least 24. In yet other preferred embodiments, the periodicity of the uninterrupted cycles is weekly, wherein the number of doses in each cycle is 2, and more preferably 1. In some embodiments, a second drug is used in combination therapy. Folic acid is particularly preferred as the second drug.

Typically, each cycle consists of less than 0.07 mg aminopterin per kilogram of patient body weight that can be administered in less than 5 tablets. For example, a 0.25 kg patient would be administered less than 0.0175 mg aminopterin, whereas a 1.0 kg patient would be administered less than 0.07 mg aminopterin, whereas a 60 kg patient would be administered less than 4.2 mg aminopterin, and whereas a 100.0 kg patient would be administered less than 7 mg aminopterin; thus in a preferred embodiment a tablet may contain between about 0.0175 mg and about 7 mg aminopterin, preferably between about 0.0175 mg and about 0.5 mg, and most preferably between 0.025 mg and about 0.5 mg. Optimal dosing without toxicity manifestations is achieved in particularly preferred embodiments utilizing one or more tablets containing less than 0.5 mg aminopterin each.

In other embodiments, a method is provided for treating an inflammatory disorder in a patient, comprising administering to said patient a single dose of a therapeutically effective amount of an antifolate, or a pharmaceutically acceptable salt thereof. In preferred embodiments, the antifolate is aminopterin. Preferred inflammatory disorders that can be treated with a single dose of an antifolate include human bronchopulmonary dysplasia, canine atopic dermatitis, bovine acute pneumonic pasteurellosis, SLE, GVHD and polymyositis. Canine atopic dermatitis is one of the most common conditions seen by veterinarians, and bovine acute pneumonic pasteurellosis, also known as 'shipping fever' in transported cattle costs the cattle industry $1 billion per year (Malazdrewich, et al. *Vet. Pathol.* 38:297, 2001). In shipping fever, the ability to treat affected animals with a minimum number of drug administrations has critical economic advantages.

In other embodiments, a method is provided for treating an inflammatory disorder in a patient, comprising administering to said patient a therapeutically effective amount of aminopterin, or a pharmaceutically acceptable salt thereof, wherein the inflammatory disorder is SLE, GVHD or polymyositis.

In other embodiments, a method is provided for treating an inflammatory disorder in a patient, comprising administering to said patient a therapeutically effective amount of aminopterin, or a pharmaceutically acceptable salt thereof wherein the inflammatory disorder is selected from MS and asthma.

In other embodiments, a method is provided for treating an inflammatory disorder in a patient, comprising administering to said patient a therapeutically effective amount of an antifolate, or a pharmaceutically acceptable salt thereof, wherein the inflammatory disorder is selected from the group consisting of canine atopic dermatitis, bronchopulmonary dysplasia, SLE, GVHD and polymyositis. When the antifolate is aminopterin, the therapeutically effective amount administered per week is between about 0.0005 and about 0.07 mg per kilogram of patient body weight. For example, a 0.05 kg patient would be administered between about 0.000025 mg and about 0.0035 mg aminopterin; a 0.1 kg patient would be administered between about 0.00005 mg and about 0.007 mg aminopterin; a 0.25 kg patient would be administered between about 0.000125 mg and about 0.0175 mg aminopterin; a 1.0 kg patient would be administered between about 0.0005 mg and about 0.07 mg aminopterin; a 60 kg patient would be administered between about 0.03 and about 4.2 mg aminopterin; and a 100 kg patient would be administered between about 0.05 mg and about 7 mg aminopterin. In preferred embodiments, the above doses are in tablet form. In another preferred embodiment, the amount of aminopterin or pharmaceutically acceptable salt thereof, within the tablet is between 0.000025 mg and about 0.5 mg, more preferably between about 0.00005 mg and about 0.5 mg, more preferably between about 0.000125 mg and about 0.5 mg. In another preferred embodiment, the amount of aminopterin, or pharmaceutically acceptable salt thereof, within the tablet is between about 0.000025 mg and about 0.5 mg, more preferably between about 0.000025 mg and about 0.45 mg, and more preferably between about 0.000025 mg and about 0.4 mg. One skilled in the art will readily recognize tablets may contain aminopterin, or a pharmaceutically acceptable salt thereof, in amounts of 0.05 mg, 0.075 mg, 0.1 mg, 0.15 mg, 0.2 mg, 0.25 mg, 0.3 mg, 0.35 mg, 0.4 mg, 0.45 mg and 0.5 mg per tablet. In another preferred embodiment, the therapeutically effective amount of the antifolate is administered in uninterrupted cycles. In another preferred embodiment, the antifolate is methotrexate and the dosages and tablet strengths of the aforementioned ranges for aminopterin are increased about 10-fold.

In other embodiments, a method is provided for treating an inflammatory disorder in a patient, comprising administering to said patient a therapeutically effective amount of aminopterin, or a pharmaceutically acceptable salt thereof, wherein the therapeutically effective amount of aminopterin administered per week is less than 0.07 mg aminopterin per kilogram of patient body weight. In this method, aminopterin is preferably administered in one or more tablets, wherein at least one tablet contains less than 0.5 mg aminopterin. For example, a 0.25 kg patient would be administered less than 0.0175 mg aminopterin; a 1.0 kg patient would be administered less than 0.07 mg aminopterin; a 60 kg patient would be administered less than 4.2 mg aminopterin; and a 100 kg patient would be administered less than 7.0 mg aminopterin; thus in a preferred embodiment, a tablet would contain aminopterin, or a pharmaceutically acceptable salt thereof, in the amount between about 0.0175 mg and about 4.2 mg, more preferably between about 0.0175 mg and about 2.0 mg, more preferably between about 0.0175 and about 1.0 mg, and most preferably between about 0.0175 mg and about 0.5 mg. One skilled in the art will readily recognize tablets may contain aminopterin, or a pharmaceutically acceptable salt thereof, in amounts of 0.05 mg, 0.1 mg, 0.2 mg, 0.3 mg, 0.4 mg, and 0.5 mg per tablet.

In other embodiments, a method is provided for treating an inflammatory disorder in a patient, comprising administering to said patient a therapeutically effective amount of aminopterin, or a pharmaceutically acceptable salt thereof, wherein the inflammatory disorder is treated more rapidly than with methotrexate. The rate of treatment is quantified with a disease manifestation scoring system selected from the group consisting of ACR20, ACR50, ACR70, ACR-N, JRA30% DOI, JRA50% DOI, JRA70% DOI, PASI, pulmonary function testing, oxygen saturation, lesional scores, Kurtzke's expanded disability status scale (EDSS), and pruritis scores. In other embodiments, the rate of treatment is quantified by the area under the efficacy-time curve.

In other embodiments, a pharmaceutical composition is provided comprising a therapeutically effective amount of aminopterin, or a pharmaceutically acceptable salt thereof, wherein the pharmaceutical composition contains less than 0.5 mg aminopterin. The pharmaceutical composition is preferably a tablet, and in certain embodiments is a 0.05 mg, 0.075 mg, 0.1 mg, 0.15 mg, 0.2 mg, 0.25 mg, 0.3 mg, 0.35 mg, 0.4 mg, or 0.45 mg tablet. In a particularly preferred embodiment, the active pharmaceutical ingredient is substantially free of impurities.

These and other aspects will become apparent upon reference to the detailed description and illustrative examples which are intended to exemplify non-limiting embodiments. All references disclosed herein are hereby incorporated by reference in their entirety as if each was incorporated individually.

GLOSSARY

Figure 1:
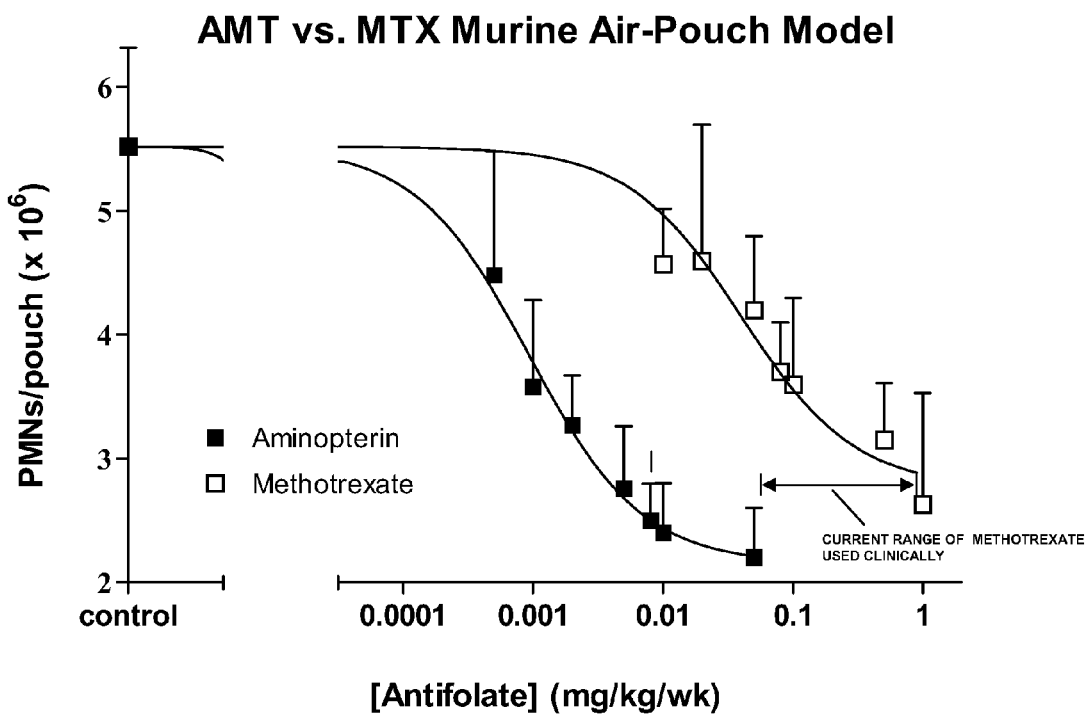
FIG. 1 is a dose-response plot of aminopterin and methotrexate in the murine air-pouch model of inflammation.

Prior to setting forth detail, it may be helpful to an understanding thereof to set forth definitions of certain terms that will be used hereinafter.

The term "active pharmaceutical ingredient" as used herein means a mixture of an antifolate and impurities resulting from one or more organic synthetic steps. An organic synthetic step will comprise the partial or complete transformation of one or more chemicals to one or more new chemicals, and will also usually entail at least one or more purification steps to enrich the one or more new chemicals. The one or more purification steps will consist of methods known to those skilled in the art, such as, for example, crystallization, extraction, and chromatography. Ideally, purification steps are not required, or the one or more purification steps will enrich a single new chemical preferentially. For example, an active pharmaceutical ingredient containing aminopterin is made by the transformation of 2,4-diamino-6-(bromomethyl)pteridine and N-(4-aminobenzoyl)-L-glutamic acid in dimethylacetamide to aminopterin plus several impurities, wherein the impurities comprise at least folic acid and untransformed 2,4-diamino-6-(bromomethyl)pteridine and N-(4-aminobenzoyl)-L-glutamic acid.

The term "aminopterin purity" as used herein means the percentage of antifolate in an active pharmaceutical ingredient or pharmaceutical composition, wherein the antifolate is aminopterin (see glossary definition of "impurities").

The term "antifolate" as used herein means a molecule and/or metabolites of the molecule that interfere with the normal metabolism or utilization of folic acid (i.e. folate) and/or metabolites of folic acid in a cell-free biochemical system or in cells found in cell culture, tissue culture, leukemia, cancer, a mammal, and a human. For example, aminopterin and methotrexate, as well as their polyglutamated metabolites, are antifolates. Typically, an antifolate and/or metabolite of the antifolate will interfere with the normal metabolism or utilization of folic acid and/or metabolites of folic acid by blocking their binding to one or more enzymes or receptors that include, for example, the reduced folate receptor, the folic acid receptor, folylpolyglutamate synthase, dihyrofolate reductase, thymidylate synthase, methylene-tetrahydrofolate reductase, amido phosphoribosyltransferase, glycinamide ribonucleotide transformylase, aminoimidazole carboxamide ribonucleotide transformylase, and homocysteine methyltransferase. Examples of folic acid metabolites that an antifolate and/or metabolites of the antifolate will interfere with include, but are not limited to, 5-methyl-tetrahydrofolate-(glu)$_n$, 5,10-methylene-tetrahydrofolate-(glu)$_n$, tetrahydrofolate-(glu)$_n$, N-5-fomamino-tetrahydrofolate-(glu)$_n$, 5,10-methenyl-tetrahydrofolate-(glu)$_n$, 10-formyl-tetrahydrofolate-(glu)$_n$, and 5-formyl-tetrahydrofolate-(glu)$_n$, where -(glu)$_n$ refers to the glutamates attached to the metabolite and n is the number of attached glutamates. When n=1, no glutamates have been added to these folic acid metabolites beyond that found in the original folic acid molecule. When n is greater than 1 these folic acid metabolites are considered to be polyglutamates (see glossary term below).

The term "AUC" as used herein means the area under the plasma concentration-time curve for a single dose of a drug as described more fully in Shargel and Yu, *Applied Biopharmaceutics and Pharmacokinetics*, 4$^{th}$ Edition, 1999, Appleton & Lange, Stamford, Conn., incorporated herein by reference. The AUC is proportional to the amount of drug that reaches the plasma.

The term "combination therapy" as used herein refers to the use of two or more therapeutics according to a therapeutic protocol with the aim of providing a highly optimized treatment plan to most effectively treat an inflammatory disorder in a patient.

The term "disease manifestation" as used herein refers to any undesired result of an inflammatory disorder. Particular disease manifestations include, but are not limited to lethargy, joint pain, joint inflammation, joint damage, inflammatory cells in joint fluid, and psoriatic skin lesions. Disease manifestations are often quantified in the art using well known scoring systems, such as for example, ACR20, ACR50, ACR70 or ACR-N in rheumatoid arthritis (Felson et al., *Arthritis Rheum.* 38:727, 1995; Bathon et al., *N. Engl. J. Med.* 343:1586, 2000; and William St. Clair et al., *Arthritis Rheum.* 50(11):3432-3443, 2004); JRA30% DOI, JRA50% DOI and JRA70% DOI in juvenile rheumatoid arthritis (Giannini et al., *Arthritis Rheum.* 40(7):1202-1209, 1997; and Lovell et al., *Arthritis Rheum.* 48(1):218, 2003), the PASI (Psoriasis Activity and Severity Index) score inpsoriasis (Finlay et al., *Br. J. Dermatol.* 123:751, 1990); pulmonary function testing and oxygen saturation in bronchopulmonary dysplasia and asthma; lesional and pruritis scores in canine atopic dermatitis (Olivry and Mueller, *Veterinary Dermatol.* 14:121-146, 2004); Kurtzke's expanded disability status scale (EDSS) (Kurtzke J. F., *Neurology.* 33:1444-52, 1983) in multiple sclerosis; the gradings of GVHD are according to accepted criteria (Thomas et al., *New Engl. J. Med.* 292:832-843, 895-902, 1975); the group classifications of polymyositis (Holden et al., *Can. Med. Assoc. J.* 132:Mar. 15, 1985; Bohan A., and Peter, J. B., *New Engl. J. Med.* 292:344-347, 1975). Other ways of quantifying disease manifestations in a patient with an inflammatory disorder will be familiar to those skilled in the art.

The term "efficacy" as used herein means an antifolate is therapeutically effective. Generally, a greater level of efficacy will be achieved by increasing the dose and/or frequency of administration of an antifolate given to a population, such that a greater proportion of the population will receive a benefit and/or there will be a greater magnitude of benefit in an individual patient. If a first antifolate is more potent than a second antifolate, it will reach a greater level of efficacy than the second antifolate using identical amounts of each.

The term "impurities" as used herein refers to the impurities found in the active pharmaceutical ingredient. Impurities arise during the organic synthetic steps employed in the preparation of the active pharmaceutical ingredient, and in the case of aminopterin include, for example, folic acid, pterins, and conjugates of p-aminobenzoic acid (i.e. pABAglu). Impurities may be the result of incomplete transformation of chemicals during an organic synthetic step, or one or more side-reactions that result in chemicals being transformed into unintended new chemicals. As defined herein, the pharmaceutically acceptable carriers and optional therapeutic ingredients in a pharmaceutical composition do not constitute impurities. Impurities in a pharmaceutical composition pertain only to those impurities in the active pharmaceutical ingredient used to make the pharmaceutical composition. Impurities are quantitated using any measurable property suitable for quantitating molecules. Such measurable properties will be familiar to those in the art and include, for example, HPLC peak area (i.e. "area"), mass and moles. Impurities will typically be conveniently quantitated based on their area, but may also be quantitated according to their weight or moles using, for example, uv absorbance of collected HPLC peak fractions and the known extinction coefficient and molecular weight of each impurity. If the molecular weight of an impurity is unknown, mass spectrometry may be used. The percentage of an impurity in an active pharmaceutical ingredient or pharmaceutical composition is the amount of the impurity divided by the total amount of impurities plus antifolate multiplied by 100, wherein all impurities and the antifolate are quantitated using the same measurable property. For example, the percentage of an impurity in an active pharmaceutical ingredient or pharmaceutical composition may be expressed as an area %, weight %, or mole %. In a specific example, if an impurity constitutes 0.1 micromole of an active pharmaceutical ingredient and the aminopterin plus total impurities in the active pharmaceutical ingredient together constitute 1 micromole, the percentage of the impurity in the active pharmaceutical ingredient is 10 mole %. In another example, if an impurity is 0.25 area units of a pharmaceutical composition and the total impurities plus antifolate together are 1.0 area units of the pharmaceutical composition, the percentage of the impurity in the pharmaceutical composition (or the active pharmaceutical ingredient) is 25 area %. In a further example, if an impurity is 0.04 mg of a pharmaceutical composition containing 2 mg of the active pharmaceutical ingredient, the percentage of the impurity in the pharmaceutical composition is 2 weight %. The percentage of total impurities may be obtained by summing the percentages of all individual impurities in the active pharmaceutical ingredient or pharmaceutical composition, wherein all the individual impurities are quantitated using the same measurable property. The percentage of antifolate in an active pharmaceutical ingredient or pharmaceutical composition is the amount of antifolate divided by the total amount of impurities plus antifolate multiplied by 100, wherein all impurities and the antifolate are quantitated using the same measurable property. Thus, the percentage of total impurities in the active pharmaceutical ingredient or pharmaceutical composition may alternatively be obtained by subtracting the percentage of antifolate from 100%.

The term "oral bioavailability" as used herein refers to the fraction of an antifolate dose given orally that is absorbed into the plasma after a single administration to a patient. A preferred method for determining the oral bioavailability is by dividing the AUC of an antifolate dose given orally by the AUC of the same antifolate dose given intravenously to the same patient, and expressing the ratio as a percent. Other methods for calculating oral bioavailability will be familiar to those skilled in the art, and are described in greater detail in Shargel and Yu, *Applied Biopharmaceutics and Pharmacokinetics*, $4^{th}$ Edition, 1999, Appleton & Lange, Stamford, Conn., incorporated herein by reference.

The term "patient" is an animal or a human.

The term "pharmaceutical composition" as used herein means the active pharmaceutical ingredient combined with one or more pharmaceutically acceptable carriers, and optionally other therapeutic ingredients. Suitable pharmaceutically acceptable carriers will be familiar to those skilled in the art, and will comprise, for example, microcrystalline cellulose, lactose, silicon dioxide, croscarmellose, sodium benzoate, sorbitol, magnesium stearate and flavoring. The active pharmaceutical ingredient will typically comprise only a small percentage of the total pharmaceutical composition. For example, a "2 mg aminopterin tablet" is a pharmaceutical composition that weighs about 100 mg, and comprises about 98 grams of pharmaceutically acceptable carriers and about 2 mg of the active pharmaceutical ingredient. The 2 mg of the active pharmaceutical ingredient consists mostly of aminopterin and a small fraction of impurities (see glossary definition of "impurities" and "active pharmaceutical ingredient"). If this pharmaceutical composition is said to be "substantially free of impurities", then the small fraction of impurities will be, for example, less than 5 area %, less than 5 weight %, or less than 5 mole % percent of the active pharmaceutical ingredient (see glossary definition of "substantially free of impurities").

The term "percent inhibition" as used herein refers to the percent of DHFR molecules bound by antifolate; aminopterin or methotrexate. The DHFR molecules on which the percentage is calculated may be those from within the entire patient, or those from within a particular representative sampled subfraction of the patient (e.g. a particular organ such as the liver, blood, bone marrow, etc.).

The term "polyglutamates" as used herein refers to folate and antifolate metabolites that have attached two or more glutamates. The enzyme folylpolyglutamate synthase attaches additional glutamates to folate metabolites and some antifolates beyond the glutamate that is on the original folate metabolite and some antifolates to form a polyglutamate chain. Examples of aminopterin and methotrexate polyglutamates include aminopterin-$(glu)_n$ and methotrexate-$(glu)_n$, where -$(glu)_n$ refers to the glutamates attached to the antifolate and n is the number of attached glutamates. When n=1, no glutamates have been added beyond that in the original antifolate molecule. When n is greater than 1 these antifolates are considered to be polyglutamates, and thus have a polyglutamate chain. A polyglutamate chain is said to have a length, wherein a first polyglutamate chain is said to have a longer length than a second polyglutamate chain if the n of the first polyglutamate chain is larger than the n of the second polyglutamate chain. Folate and antifolate metabolites having polyglutamate chains are often referred to as polyglutamated species or polyglutamates. A mixture of polyglutamate chains having different lengths is said to comprise polyglutamate chain lengths. Both aminopterin and methotrexate are metabolized to polyglutamates having an n of from 2 to about 5, as described in greater detail in, Gangjee et al., *Curr. Med. Chem. Anti-Canc. Agents.* 2(3):331, 2002, incorporated herein by reference.

The term "potency" as used herein means the effectiveness of a dosage to achieve a particular level of efficacy. The dosage takes into account the amount of drug given at each administration (i.e. dose), the frequency of administration, and optionally, the total number of doses to be given. The effectiveness of a dosage can be quantitated by measuring the cumulative amount of drug administered in a defined period (i.e. the "dose rate") of the dosage and that results in a particular level of efficacy, where effectiveness and potency are inversely related to the dose rate. A first drug whose dosage has greater effectiveness or potency than the dosage of a second drug is said to be more potent than the second drug. For example, a first antifolate is more potent than a second antifolate if both achieve the same level of efficacy using a dose rate that is smaller in the first antifolate than the second antifolate. In a more specific example, a first antifolate is more potent than a second antifolate if both achieve the same level of efficacy using a dosage that is identical except for the dose of the first antifolate being smaller than the dose of the second antifolate. In a further example, a first antifolate is more potent than a second antifolate if both achieve the same level of efficacy using a dosage that is identical except for the frequency of administration of the first antifolate being smaller than the frequency of administration of the second antifolate. Two different antifolates may have different potencies, and will therefore achieve the same level of efficacy at different therapeutically effective amounts. For example, aminopterin is about 25 times more potent than methotrexate, and therefore the therapeutically effective amount of aminopterin required for a level of efficacy is about 25-fold less than the therapeutically effective amount of methotrexate required for the same level of efficacy. The therapeutically effective amounts of two antifolates (i.e. either as a dosage or as a single dose) that result generally in the same level of efficacy are referred to herein as equi-potent. For example, two oral doses of 2 mg/m$^2$ aminopterin are approximately equi-potent to four oral doses of 25 mg/m$^2$ methotrexate.

The term "substantially free of impurities" as used herein means that the percentage of total impurities in an active pharmaceutical ingredient or in a pharmaceutical composition is less than five percent (see definition of "impurities"). For example, a pharmaceutical composition or active pharmaceutical ingredient is said to be substantially free of impurities if the percentage of total impurities is less than 5 area %, 5 weight % or 5 mole %. As used herein, "substantially free of impurities" also means that the percentage of antifolate in an active pharmaceutical ingredient or in a pharmaceutical composition is ninety-five percent or greater (see definition of "impurities"). For example, a pharmaceutical composition that has a percentage of antifolate with an area %, weight %, or mole % equal to or greater than ninety-five, is said to be substantially free of impurities. In a more specific example, a pharmaceutical composition or active pharmaceutical ingredient that has an aminopterin purity with an area %, weight %, or mole % equal to or greater than ninety-five, is said to be substantially free of impurities.

The term "therapeutic component" as used herein refers to a therapeutically effective dosage (i.e. dose and frequency of administration) that eliminates, reduces, or prevents the progression of a particular disease manifestation in a percentage of a population. An example of a commonly used therapeutic component is the $ED_{50}$, which describes the dose in a particular dosage that is therapeutically effective for a particular disease manifestation in 50% of a population.

The term "therapeutic index" as used herein refers to the ratio of a particular toxicity component (i.e. the dose that is toxic in a percentage of a population, for example, the $TD_{50}$) to a particular therapeutic component (i.e. the dose that is effective in percentage of a population, for example, the $ED_{50}$). It will be understood by a skilled practitioner that the determination of the therapeutic index of an antifolate, such as aminopterin, need not be determined for every patient in a population with a inflammatory disorder treated according to the disclosure. It is sufficient to use a representative number of patients with the inflammatory disorder to establish a therapeutic index for the entire patient population with the inflammatory disorder, where at least 5 patients with the inflammatory disorder will be required in order to establish a therapeutic index for the entire patient population with the inflammatory disorder.

The term "therapeutic protocol" as used herein refers to a schedule of dosing, routes of administration, and schedule duration for two or more drugs that are employed within combination therapy. The schedule may be further divided into specific phases each of a specified duration. For example, the phases of modern rheumatoid arthritis treatment involving the treating with NSAIDs and various other small-molecule or biologic DMARDS either sequentially or together constitute specific phases of a therapeutic protocol. During each phase, the type of drugs to be given, their dosing, and routes of dosing are defined for all patients in general or may be modified based on other disease factors such a laboratory or imaging tests.

The term "therapeutically effective amount" as used herein means the dosage (dose or amount, and frequency) of antifolate which directly or indirectly kills inflammatory cells, arrests the accumulation of inflammatory cells, or reduces the accumulation of inflammatory cells in a human or other mammal afflicted with an inflammatory disorder (i.e. a patient) such as, for example, arthritis of undefined etiology, rheumatoid arthritis, juvenile rheumatoid arthritis, atopic dermatitis, bronchopulmonary dysplasia, asthma, multiple sclerosis, inflammatory bowel disease, psoriatic arthritis, SLE, GVHD, polymyositis and psoriasis, or a animal with, for example, canine atopic dermatitis or bovine acute pneumonic pasteurellosis. The term as used herein shall also mean the dosage of an antifolate which directly or indirectly reduces or increases the activity of molecules secreted by inflammatory and/or non-inflammatory cells participating in an inflammatory disorder in a human or mammal, such that the amount of antifolate arrests, reduces, or eliminates altogether the degree of pathologic inflammation associated with the inflammatory inflammatory disorder. Typically, a therapeutically effective amount will also eliminate, reduce, or prevent the progression of, one or more disease manifestations. A skilled artisan readily recognizes that in many cases antifolates may not provide a cure, but may only provide partial benefit. Furthermore, the skilled artisan recognizes that because individual patients and disease states may vary, some patients may receive little or no benefit at all. A dosage of antifolate that "kills", "arrests", "reduces" or "eliminates" as described above, in a least some patients, is considered therapeutically effective. The dose magnitude of a therapeutically effective amount of aminopterin in the acute or chronic management of a inflammatory disorder will vary with the severity of the inflammatory disorder to be treated and the route of administration. The dosage and dose rate of aminopterin will depend on a variety of factors, such as the weight and calculated surface area of the patient, the specific pharmaceutical composition used, the object of the treatment, i.e., therapy or prophylaxis, the nature of the disease to be treated, the judgment of the treating physician, and the response of the individual patient. In general, a therapeutically effective amount of aminopterin will be a dose of aminopterin from 0.001-0.07 mg/kg, 0.005-0.03 mg/kg, and most preferably 0.010-0.03 mg/kg, given as a single or divided dose. Thus, for example, the therapeutically effective amount of aminopterin, or pharmaceutically acceptable salt thereof, given as a single or divided dose, for a 0.25 kg patient would range between 0.00025-0.0175 mg, 0.00125-0.0075 mg, and most preferably 0.0025-0.0075 mg; whereas for a 1.0 kg patient the therapeutically effective amount of aminopterin would range between 0.001-0.07 mg, 0.005-0.03 mg, and most preferably 0.010-0.03 mg; whereas the therapeutically effective amount of aminopterin for a 60 kg patient would range between 0.06-4.2 mg, 0.3-1.8 mg, and most preferably 0.6-1.8 mg aminopterin; whereas the therapeutically effective amount of aminopterin for a 100 kg patient would range between 0.1-7 mg, 0.5-3 mg, and most preferably 1-3 mg aminopterin. Thus, the amount of aminopterin, or pharmaceutically acceptable salt thereof, within the tablet could thus range between 0.00025-7.0 mg, more preferably between 0.00025-2.0 mg, more preferably between 0.00025-0.5 mg, more preferably between 0.0025-0.5 mg, more preferably between 0.025-0.5 mg. As encompassed by these ranges, one skilled in the art will readily recognize tablets may contain aminopterin, or a pharmaceutically acceptable salt thereof, in amounts of 0.05 mg, 0.075 mg, 0.1 mg, 0.15 mg, 0.2 mg, 0.25 mg, 0.3 mg, 0.35 mg, 0.4 mg, 0.45 mg and 0.5 mg per tablet.

Patients may be upward titrated from below to within these dose ranges to a satisfactory control of disease manifestations. Once improvement in the patient's condition has occurred, a maintenance dosage of a composition of this disclosure is administered, if necessary. Subsequently, the dose rate may be reduced by reducing the dose or frequency of administration, or a combination of both, as a function of the symptoms, to a level at which the improved condition is retained. When the symptoms have been alleviated to the desired level, the practitioner may elect to cease treatment. Patients may, however, require intermittent treatment upon any recurrence of disease symptoms, or prophylactically scheduled treatments as required. The therapeutically effective amount of aminopterin may optionally be administered prior to, contemporaneous with, or after at least one therapeutically effective dose of leucovorin or folic acid.

The term "toxicity component" as used herein refers to the dosage (i.e. dose and frequency of administration) required to produce a toxicity manifestation in a percentage of a population. An example of a commonly used toxicity component is the $TD_{50}$, which describes the dose in a particular dosage required to produce a toxicity manifestation in 50% of a population. Generally, there is an inverse relationship between dose and frequency necessary to produce the same toxicity component, where less antifolate given more often will produce the same toxicity component as more antifolate given less often.

The term "toxicity manifestation" as used herein refers to any undesired effect of a drug. A drug is said to be toxic or have toxicity if it causes a toxicity manifestation in a percentage of a population. For antifolates, particular toxicity manifestations include, but are not limited to mucositis, alopecia, diarrhea, myelosuppression, nephrotoxicity, hepatotoxicity, severe hepatotoxicity, neurotoxicity, and death. Toxicity manifestations also include indirect indications of toxicity such as thrombocytopenia (e.g. <50,000 µL), neutropenia (e.g. <750 µL), elevated liver enzymes (e.g. >5 times normal), erythrocyte antifolate (e.g. eAMT and eMTX), the necessary discontinuation of therapy by a patient because of the inability to endure further treatment with the drug, or increased hospital admissions due to the inability to continue therapy. Thus, a practitioner can assess the presence and the magnitude of a particular toxicity manifestation. Many, if not all, of the toxicity manifestations of antifolates can be reversed by the prior, contemporaneous or subsequent administration of leucovorin, a reduced folate that is well known in the art to rescue antifolate toxicity.

DETAILED DESCRIPTION

Embodiments described herein provide dosages and methods for treating a patient with an inflammatory disorder with a therapeutically effective amount of aminopterin, or a pharmaceutically acceptable salt, that provide unexpected advantages of patient convenience while also achieving efficacy without concomitant toxicity. The inflammatory disorder may occur in humans and comprise, for example, arthritis of undefined etiology, rheumatoid arthritis, psoriatic arthritis, juvenile rheumatoid arthritis, psoriasis, inflammatory bowel disease, asthma, multiple sclerosis, atopic dermatitis, SLE, GVHD, polymyositis and bronchopulmonary dysplasia. The animal inflammatory disorder may occur in animals and comprise, for example, arthritis, canine atopic dermatitis and bovine acute pneumonic pasteurellosis.

Although not to be limited by theory, aminopterin inhibits enzymes involved in purine and pyrimidine metabolism, including DHFR, that leads indirectly to the extracellular release of adenosine.

DHFR is said to be inhibited in a patient if the percent inhibition comprises the range of 5% to 100%. In some embodiments, the percent inhibition of DHFR in a patient during each dosing cycle of a therapeutically effective amount of aminopterin is greater than 5%, 10%, 20%, 30%, 40%, 50%, 60%, 70%, 80% and 90%. In other embodiments, the percent inhibition during each cycle of a therapeutically effective amount of aminopterin will comprise a range of DHFR inhibition, where the lower end of the range comprises percent inhibition greater than 5%, 10%, 20%, 30%, 40%, 50%, 60%, 70%, 80% and 90%; and the upper end of the range comprises percent inhibition less than 5%, 10%, 20%, 30%, 40%, 50%, 60%, 70%, 80% and 100%. In preferred embodiments, the cycle is weekly, and the range of percent inhibition of a therapeutically effective amount of aminopterin during each cycle comprises 50%-99%, 50%-95%, 50%-90%, 50%-85% and 50%-75%. In another preferred embodiment, a method is provided for inhibiting DHFR in a patient, comprising administering to said patient a therapeutically effective amount of aminopterin, or a pharmaceutically acceptable salt thereof, wherein the therapeutically effective amount of aminopterin, or pharmaceutically acceptable salt thereof, administered per week is between 0.0005 and 0.07 mg per kilogram of patient body weight. In further embodiments, the aminopterin is administered in uninterrupted cycles.

Adenosine is a powerful anti-inflammatory autocoid that regulates innate immunity (reviewed by Hasko and Cronstein, (2004) Adenosine: an endogenous regulator of innate immunity. *Trends Immunol.*, 25/1:33-39) and that decreases the activation of antigen-stimulated cells, decreases the expression of adhesion molecules, and possibly induces T cell apoptosis (Cronstein, et al., *Proc. Natl. Acad. Sci. USA* (1991), 88: 2441; Cronstein, et al., *J. Clin. Invest.* (1993), 92/6:2675; Genesteir, et al., *J. Clin. Invest.* (1998), 102:322-328; Morabito, et al., *J. Clin. Invest.* (1998), 101:295-300; Paillot et al., *Transplant Proc.* (1998), 30/5:2348-50; Johnston et al., *Clin. Immunol.* (2005), 114/2:154-63). The pivotal role of adenosine in human inflammatory disorders such as rheumatoid arthritis and psoriasis is now appreciated. Adenosine can be measured directly in the synovial fluid collected from patients with rheumatoid arthritis (Ottonello et al., *Rheumatology* (2002), 41:1249-1260).

Thus, in one embodiment, a method is provided for treating a patient having an inflammatory disorder inhibited by the release of adenosine, wherein the method comprises administering to said patient in need thereof a therapeutically effective amount of aminopterin, or a pharmaceutically acceptable salt thereof. Inflammatory disorders that may be inhibited by the release of adenosine are readily identified by methods readily available to those skilled in the art. In one method for identifying an inflammatory disorder inhibited by the release adenosine, an adenosine receptor knockout (e.g. $A_{2A}$ and/or $A_3$ adeonsine receptors) animal is prepared, wherein there exists a model of a human or animal inflammatory disorder (Montesinos et al. (2003) *Arthritis Rheum.*, 48/1:240-247). Aminopterin is then administered to control (e.g. wild type) animals and the knockout animals, wherein both have the inflammatory disorder (e.g. carrageenan-induced inflammation in the mouse air-pouch model of inflammation).

The inflammatory disorder is said to be inhibited by the release of adenosine if the 'therapeutic component' (see Glossary above) in the control animals is at least 2, 5, and more preferably, at least 10 times less than in the knockout animals. In many embodiments, no therapeutically effective amount will exist in the knockout animals (i.e. they are completely insensitive to the therapeutic effects of aminopterin). It will be appreciated that this method allows the adenosine receptor isoform involvement in the disorder to be characterized.

In another method for identifying an inflammatory disorder inhibited by the release adenosine, control and test groups of animals or humans with an inflammatory disorder are both administered aminopterin as described herein. The test group is then administered an inhibitor of adenosine binding to one or more adenosine receptors. Some inhibitors will be selective for particular adenosine receptor isoforms, and this will permit isoform involvement in the disorder to be characterized. Suitable inhibitors of adenosine receptor binding include, but are not limited to, caffeine, DPCPX, PACPX, ZM241385, CSC, alloxane, and MRS-1220 (as defined in Hasko and Cronstein, (2004) Adenosine: an endogenous regulator of innate immunity. *Trends Immunol.*, 25/1:33-39).

The inflammatory disorder is said to be inhibited by the release of adenosine if the 'therapeutic component' (see Glossary above) in the control animals is at least 2, 5, and more preferably, at least 10 times less than in the test group administered the inhibitor of adenosine receptor binding. In many embodiments, no therapeutically effective amount will exist in the group administered the inhibitor of adenosine receptor binding (i.e. they are completely insensitive to the therapeutic effects of aminopterin).

In still other methods for identifying an inflammatory disorder inhibited by the release adenosine, control and test groups of animals or humans with an inflammatory disorder are both administered an agonist of one or adenosine receptors (i.e. a mimic of adenosine). Some agonists will be selective for particular adenosine receptor isoforms, and this will permit isoform involvement in the disorder to be characterized. Suitable agonists of adenosine receptors include, but are not limited to, CPA, CCPA, CGS-21680, IB-MECA and 2Cl-IB-MECA (as defined in Hasko and Cronstein, (2004) Adenosine: an endogenous regulator of innate immunity. *Trends Immunol.*, 25/1:33-39).

The inflammatory disorder is said to be inhibited by the release of adenosine if there is a 'therapeutic component' in the test group of animals, relative to the disease manifestations in the control group (see Glossary above for therapeutic component). In some embodiments, the therapeutic component will be a dose of agonist that completely eliminates, reduces, or prevents the progression of a particular disease manifestation in the test group of animals.

Within certain embodiments, the present disclosure provides a method for treating an inflammatory disorder in a patient with uninterrupted cycles of aminopterin doses, wherein the doses are a therapeutically effective amount. Uninterrupted means that aminopterin doses are repetitively administered to a patient for at least 4 cycles, 5 cycles, 10 cycles, 12 cycles, 24 cycles, 36 cycles, and most preferably greater than 52 cycles, wherein the periodicity of the cycles is constant, and wherein the greatest duration between the last dose of one cycle and the first dose of the next cycle does not exceed 21 days, 14 days, and most preferably 7 days. Within this definition, 'periodicity of the cycles is constant' means that the duration between corresponding doses in consecutive cycles is constant to within a 12 hour range. For example, if the periodicity is denoted to be 7 days (i.e. 168 hours), then according to the present disclosure the phrase 'periodicity of the cycles is constant' will be construed to mean that the duration between corresponding doses in consecutive cycles may range from 162 to 174 hours. Further within this definition, the number of aminopterin doses in each cycle can range from 1 to 5, and each individual dose may comprise taking one or a plurality of individual dosage forms.

Thus, in a preferred embodiment 1 dose of aminopterin is administered to a patient every 7 days for at least 4 cycles, and most preferably for at least 52 cycles (i.e. a year). In this case, the number of doses per cycle is only a single dose, the periodicity is 7 days, and the greatest duration between the last dose of one cycle and the first dose of the next cycle is 6 days. In another preferred embodiment one dose of aminopterin is administered on Monday and one on Tuesday for at least 52 cycles. In this case, the number of doses per cycle is 2, the periodicity is 7 days, and the greatest duration between the last dose of one cycle and the first dose of the next cycle is 5 days (i.e. Wednesday through Sunday). In yet another preferred embodiment, a dose of aminopterin is administered in the morning and another at night on a particular day of the week by taking two tablets with each dose, this cycle is then repeated for at least 52 cycles. In this case, the number of doses per cycle is 2 where each dose comprises taking 2 dosage forms, the periodicity is 7 days, and the greatest duration between the last dose of one cycle and the first dose of the next cycle is 6 days (i.e. the days between the day of the week the doses is given). It will be understood that other schedules are within the embodiments of the disclosure. For example, in one embodiment, one dose of aminopterin is administered on Monday and one on Wednesday for at least 52 cycles. In this case, the number of doses per cycle is 2, the periodicity is 7 days, and the greatest duration between the last dose of one cycle and the first dose of the next cycle is 4 days (i.e. Thursday through Sunday). In the most preferred embodiment, the periodicity is weekly (i.e. 7 days).

In other embodiments, methods are provided for treating an inflammatory disorder in a patient comprising administering a single cycle of aminopterin in a therapeutically effective amount. Most preferably, SLE, GVHD and polymyositis in a human patient is effectively treated with a single cycle of aminopterin, wherein the number of doses in the cycle is 1.

In other embodiments, methods are provided for treating an inflammatory disorder in a patient comprising administering a single cycle of aminopterin in a therapeutically effective amount. Most preferably, bronchopulmonary dysplasia in a human and acute pneumonic pasteurellosis in a cow is effectively treated with a single cycle of aminopterin, wherein the number of doses in the cycle is 1.

In other embodiments, methods are provided for treating an inflammatory disorder in a patient more rapidly than it can be treated with methotrexate by administering to the patient one or more doses of aminopterin in a therapeutically effective amount. In particular, a therapeutically effective amount of aminopterin will eliminate, reduce, or prevent the progression of, one or more disease manifestations in the patient more rapidly than a therapeutically effective amount of methotrexate. While the rate to reach a particular efficacy can be achieved more rapidly with aminopterin than with methotrexate in some embodiments, it will be understood that the final maximum level of efficacy achieved may be the same or different. In preferred embodiments, the final level of efficacy achieved will be greater for aminopterin than for methotrexate, in addition to this level being reached more rapidly by aminopterin. The rate can be measured using any quantitative endpoint of disease activity (see 'disease manifestation' and 'therapeutically effective amount' in the Glossary). In preferred embodiments, the rate is quantified as a function of time by measuring any of the following scoring system: ACR20, ACR50, ACR70, ACR-N, JRA30% DOI, JRA50% DOI, JRA70% DOI, PASI, pulmonary function testing, oxygen saturation, lesional scores, and pruritis scores. In other preferred embodiments, the rate is quantified by documenting an increase in the area under the 'efficacy-time curve', wherein the curve is established by plotting the output parameter of the scoring system as a function of time {see for example, Bathon et al., N. Engl. J. Med. 343:1586, 2000 for an example of this approach). The area under the efficacy-time curve is not to be confused with the 'AUC' defined in the Glossary for the area under the plasma concentration-time curve for a single dose of a drug.

In still further embodiments the weekly dosage comprises a cumulative dose of aminopterin ranging from 0.001-0.07 mg/kg, 0.005-0.03 mg/kg, and most preferably 0.010-0.03 mg/kg. For example, a 0.25 kg patient would be administered between 0.00025 mg and 0.0175 mg aminopterin, between 0.00125 mg and 0.0075 mg aminopterin, and between 0.0025 mg and 0.0075 mg aminopterin; whereas a 1.0 kg patient would be administered between 0.001 mg and 0.07 mg aminopterin, between 0.005 mg and 0.03 mg aminopterin, and between 0.01 mg and 0.03 mg aminopterin; whereas a 100 kg patient would be administered between 0.1 mg and 7.0 mg aminopterin, between 0.5 mg and 3.0 mg aminopterin, and between 1.0 mg and 3.0 mg aminopterin. For a typical 60 kg adult, the weekly dosage thus comprises a cumulative dose of aminopterin ranging from 0.06-4 mg, 0.3-1.8 mg, and most preferably 0.6-1.8 mg. In other preferred embodiments, the dosage form contains 0.05 mg, 0.75 mg, 0.1 mg, 0.15 mg, 0.2 mg, 0.25 mg, 0.3 mg, 0.35 mg, 0.4 mg, 0.45 mg, 0.5 mg, 0.55 mg, 0.6 mg, 0.65 mg, 0.7 mg, 0.75 mg, 0.8 mg, 0.85 mg, 0.9 mg, 095 mg or 1.0 mg aminopterin or therapeutically acceptable salt thereof. In still other embodiments the dosage form is a tablet. In another embodiment, the weekly dosage comprises taking one to three dosage forms by mouth of any dose combination thereof. The above cumulative weekly dose of aminopterin can be given either in a single administration at a particular time, or as a plurality of administrations during a single day, or over multiple days. Using the methods of the instant disclosure, it has been discovered that aminopterin can be given to a patient with an inflammatory disorder without toxicity manifestations, and in the most preferred embodiments without interruption. In another preferred embodiment, the amount of aminopterin, or pharmaceutically acceptable salt thereof, within a dosage form is between 0.00025 mg and 7.0 mg aminopterin, more preferably between 0.00025 mg and 0.5 mg aminopterin, more preferably between 0.00025 mg and 0.4 mg aminopterin, more preferably between 0.00025 mg and 0.3 mg aminopterin, more preferably between 0.00025 mg and 0.2 mg aminopterin, and more preferably between 0.00025 mg and 0.1 mg aminopterin. In preferred embodiments the dosage form is a tablet.

When aminopterin is administered at the above disclosed cycles and dosages, DHFR is inhibited in a patient and an amount of adenosine is released to inhibit an inflammatory disorder.

Embodiments of the present disclosure further provide methods for treating an inflammatory disorder in a patient using combination therapy, which comprises administering to said patient a therapeutically effective amount of aminopterin, or a pharmaceutically acceptable salt thereof, according to a therapeutic protocol involving at least one other therapeutic. The at least one other therapeutic may be administered prior to, contemporaneous with, or after administering the aminopterin. The at least one other therapeutic also includes a single dosage form containing aminopterin and at least one other therapeutic, a multiple dosage form, wherein the aminopterin and the at least one other therapeutic are administered separately, but concurrently, or a multiple dosage form wherein the two components are administered separately, but sequentially. The at least one other therapeutic can be, for example, folic acid, leucovorin, dextromethorphan, memantine, prednisone, a cox-2 inhibitor, a non-steroidal anti-inflammatory drug, vincristine, dexamethasone, asparaginase, daunorubicin, mercaptopurine, etoposide, cytarabine, doxorubicin, cisplatin, ifosfamide, paclitaxel, 5-fluorouracil, diahydrogalacitol, tamoxifen, piperazinedione, mitoxantrone, diaziquone, aminothiadiazole, methotrexate, tenoposide, vincristine, echinomycin, 6-mercatopurine, dexamethasone, cyclophosphamide, soluble TNF receptors, antibodies, and humanized antibodies.

In preferred embodiments, a dose of aminopterin from 0.001-0.066 mg/kg, 0.005-0.03 mg/kg, and most preferably 0.010-0.03 mg/kg, is suitable for use in a therapeutic protocol employed during a combination therapy. In some embodiments, aminopterin can be directly substituted for methotrexate in a therapeutic protocol employing methotrexate by administering aminopterin at about 4-8% of the dose of methotrexate in the protocol. This substitution yields at least the same level of efficacy and therapeutic index as methotrexate, but with far fewer tablets taken by the patient.

In one embodiment, aminopterin is substituted for methotrexate in the treatment of adult rheumatoid arthritis in a therapeutic protocol employing another non-steroidal anti-inflammatory drug by administering a single weekly oral dose of 0.5 to 2 mg aminopterin instead of a single weekly dose of 7-25 mg methotrexate. In another embodiment, aminopterin is substituted for methotrexate in the treatment of juvenile rheumatoid arthritis in a therapeutic protocol employing another non-steroidal anti-inflammatory drug by administering a single weekly oral dose of 0.5 to 2 mg aminopterin instead of a single weekly dose of 7-25 mg methotrexate. In still another embodiment, psoriasis in an adult is treated in a therapeutic protocol by administering a single weekly oral dose of 1 to 4 mg aminopterin instead of a single weekly dose of 15-25 mg methotrexate, or as two weekly oral doses of 1 to 2 mg aminopterin instead of two weekly doses of 7-13 mg methotrexate.

In another embodiment, it has been found that methotrexate, or a pharmaceutically acceptable salt thereof, is effective in treating canine atopic dermatitis and bronchopulmonary dysplasia. In a preferred embodiment, these two disorders are effectively treated with weekly doses of 7-25 mg/m² or 0.01-2 mg/kg given via oral or parenteral routes. In this embodiment of treating canine atopic dermatitis and bronchopulmonary dysplasia, methotrexate can substitute for aminopterin, as disclosed herein, using 10 to 20-fold larger doses (by weight) than aminopterin. The efficacy of methotrexate in bronchopulmonary dysplasia and canine atopic dermatitis was observed to have a slower onset than aminopterin.

An embodiment of the present disclosure further provides methods of treating an inflammatory disorder in a human, which comprises administering to said human an active pharmaceutical ingredient substantially free of impurities, wherein the antifolate in the active pharmaceutical ingredient is a therapeutically effective amount of aminopterin, or a pharmaceutically acceptable salt thereof. In some embodiments, the impurities may include, for example, folic acid, pterins, and conjugates of p-aminobenzoic acid. In preferred embodiments, the aminopterin purity in the active pharmaceutical ingredient is equal to or greater than 95 area %, equal to or greater than 95 weight %, or equal to or greater than 95 mole % (see "aminopterin purity" in glossary). In other embodiments, the active pharmaceutical ingredient has less than 5 area %, less than 5 weight %, or less than 5 mole % impurities, and more preferably less than 3 area %, less than 3 weight %, or less than 3 mole % impurities. In preferred embodiments, administering an active pharmaceutical ingredient containing an aminopterin dose from 0.03 mg/m² to about 2 mg/m², or 0.001-0.066 mg/kg will provide a therapeutically effective amount of aminopterin and will be substantially free of impurities.

The chemical synthesis of an active pharmaceutical ingredient substantially free of impurities and containing aminopterin can be performed by several different sequences of organic synthetic steps. It is understood that one of ordinary skill in the art would be able to make an active pharmaceutical ingredient substantially free of impurities and containing aminopterin in light of the following disclosure, including the Examples, and information known to those of ordinary skill in the chemical synthesis field. For example, beginning with readily available starting materials, an active pharmaceutical ingredient substantially free of impurities and containing aminopterin may be synthesized according to Scheme 1.

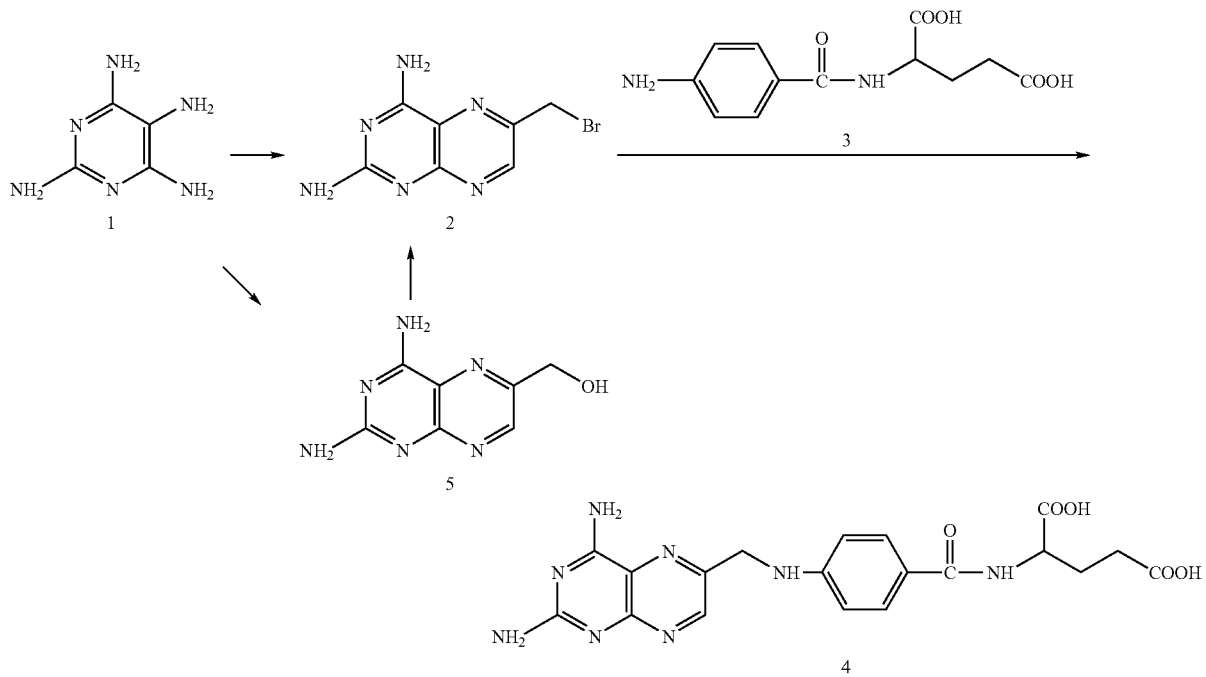

SCHEME 1

As illustrated above, the commercially available 2,4,5,6-tetraminopyrimidine, compound 1, may be condensed with β-bromopyruvaldoxime to provide 2,4-diamino-6-(bromomethyl)pteridine, compound 2 [see Taghavi-Moghadam and Pfleiderer, Tet. Lett. 38:6835, 1997 and Taylor and Portnoy, J. Org. Chem. 38:806, 1973]. Alternatively, compound 1 may be reacted with 1,3-dihydroxyacetone to provide 2,4-diamino-6-pteridinemethanol, compound 5 [see Baugh and Shaw, J. Org. Chem. 29:3610, 1964]. Compound 5 is purified and reacted with HBr and dibromotriphenylphosphorane (Ph₃PBr₂) in dimethylacetamide to afford compound 2 [see Piper and Montgomery, J. Org. Chem. 42:208, 1977; Piper and Montgomery, J. Heterocycl. Chem. 11:279, 1974; Piper and Montgomery, U.S. Pat. No. 4,077,957; and Piper and Montgomery, U.S. Pat. No. 4,079,056]. In still other embodiments, compound 2 can be arrived at via the reaction of compound 1 with 1,1-dichloroacetone to form 2,4-diamino-6-(methyl)pteridine, which is then reacted with bromide [see Catalucci, U.S. Pat. No. 4,224,446].

Regardless of the route to its synthesis, compound 2 is condensed with commercially available N-(p-aminobenzoyl)-L-glutamic acid, compound 3, in dimethylacetamide to afford the active pharmaceutical ingredient substantially free of impurities and containing aminopterin, compound 4, as the antifolate [see Piper and Montgomery, *J. Org. Chem.* 42:208, 1977; Piper and Montgomery, U.S. Pat. No. 4,077,957; Piper and Montgomery, U.S. Pat. No. 4,079,056; and Catalucci, U.S. Pat. No. 4,224,446].

In other embodiments, an active pharmaceutical ingredient substantially free of impurities and containing aminopterin as the antifolate may be obtained by purification of aminopterin preparations contaminated with impurities by, for example, ion-exchange chromatography or by HPLC [see Heinrich et al., *J. Am. Chem. Soc.* 75:5425, 1953 and Tong et al., *Lancet* 2:719, 1975]. In a preferred embodiment, an active pharmaceutical ingredient substantially free of impurities and containing aminopterin as the antifolate may be obtained by the direct transformation (i.e. amination) of folic acid to aminopterin [see Zebala, U.S. Pat. No. 7,235,660].

An embodiment of the present disclosure further provides pharmaceutical compositions substantially free of impurities and comprising an active pharmaceutical ingredient, wherein the antifolate in the active pharmaceutical ingredient is a therapeutically effective amount of aminopterin, or a pharmaceutically acceptable salt thereof. In some embodiments, the impurities may include, for example, folic acid, pterins, and conjugates of p-aminobenzoic acid. In preferred embodiments, the pharmaceutical composition has less than 5 area %, less than 5 weight %, or less than 5 mole % impurities, and more preferably less than 3 area %, less than 3 weight %, or less than 3 mole % impurities. In other embodiments, the aminopterin purity in the pharmaceutical composition is equal to or greater than 95 area %, equal to or greater than 95 weight %, or equal to or greater than 95 mole %. In preferred embodiments, a pharmaceutical composition containing from 0.2 mg to about 2.0 mg aminopterin will provide a therapeutically effective amount of aminopterin and will be substantially free of impurities. In particularly preferred embodiments, a pharmaceutical composition contains 0.5 mg aminopterin will provide a therapeutically effective amount of aminopterin and will be substantially free of impurities.

The aminopterin purity of the active pharmaceutical ingredient is used to establishe how much active pharmaceutical ingredient is required in the pharmaceutical composition to obtain a desired final dose of aminopterin, or a pharmaceutically acceptable salt thereof, in the pharmaceutical composition. For example, if a pharmaceutical composition is to contain about 1 mg of aminopterin and the aminopterin purity in the active pharmaceutical ingredient is 95 weight %, then about 1.0526 mg of the active pharmaceutical ingredient will be required in the pharmaceutical composition to provide about 1 mg of aminopterin.

In addition to the active pharmaceutical ingredient, pharmaceutical compositions substantially free of impurities contain one or more pharmaceutically acceptable carriers (see glossary definition of "pharmaceutical composition"). Pharmaceutical compositions substantially free of impurities are most readily prepared by combining an active pharmaceutical ingredient substantially free of impurities, wherein aminopterin is the antifolate in the active pharmaceutical ingredient, in intimate admixture with one or more pharmaceutical carriers according to conventional pharmaceutical compounding techniques.

The carrier may take a wide variety of forms depending on the form of the pharmaceutical composition (i.e. "preparation" or "form") desired for administration, e.g., oral, parenteral (including intravenous injections or infusions), or intrathecal. In preparing the pharmaceutical composition in an oral dosage form any of the usual pharmaceutical carriers may be employed. Usual pharmaceutical carriers include, for example, water, glycols, oils, alcohols, flavoring agents, preservatives, coloring agents, and the like in the case of oral liquid preparations (such as for example, suspensions, solutions, and elixirs); aerosols; or carriers such as starches, sugars (e.g. lactose), microcrystalline cellulose, diluents, granulating agents, lubricants, binders, disintegrating agents and the like, in the case of oral solid preparations (such as for example, powders, capsules, and tablets) with the oral solid preparations generally being preferred over the oral liquid preparations. For pediatric patients, however, it will be appreciated to those skilled in the art that pleasant tasting oral liquid preparations are preferred.

Because of their ease of administration, tablets and capsules represent the most advantageous oral dosage form in adults, in which case solid pharmaceutical carriers are employed. If desired, tablets may be coated by standard aqueous or nonaqueous techniques. The parenteral dosage form can consist of a sterile solution of the active ingredient, either in its free or salt form, in physiological buffer or sterile water. In addition, parenteral solutions can contain preservatives such as benzalkonium chloride, methyl- or propyl-paraben and chlorobutanol. Suitable pharmaceutical carriers are described in *Remington's Pharmaceutical Sciences*, a standard reference text in this field. In embodiments employing parenteral, oral liquid, or other aqueous compositions, care must be taken since electrophilic substitution by water converts aminopterin to folic acid, and such preparations have been noted to accumulate folic acid to undesirable levels over the course of six months of storage. Accordingly, such aqueous compositions are best stored desiccated and hydrated within several hours to several days prior to patient administration.

In addition to the common dosage forms set out above, the pharmaceutical compositions of the present disclosure may also be administered by controlled release means and/or delivery devices such as those described in U.S. Pat. Nos. 3,845,770; 3,916,899; 3,536,809; 3,598,123; 3,630,200; 4,008,719; 4,687,660 and 4,769,207, the disclosures of which are hereby incorporated by reference.

Optionally, the pharmaceutical composition contains other therapeutic ingredients. Such therapeutic ingredients may be added to ameliorate certain side-effects, particularly those of aminopterin, or add to patient convenience by reducing the number of dosage forms that must be taken. Suitable therapeutic ingredients for combining with the pharmaceutical composition may include, for example, folic acid, leucovorin, dextromethorphan, memantine, prednisone, a cox-2 inhibitor, a non-steroidal anti-inflammatory drug, vincristine, dexamethasone, asparaginase, daunorubicin, mercaptopurine, etoposide, cytarabine, doxorubicin, cisplatin, ifosfamide, paclitaxel, 5-fluoruracil, diahydrogalacitol, tamoxifen, piperazinedione, mitoxantrone, diaziquone, aminothiadiazole, methotrexate, tenoposide, vincristine, echinomycin, 6-mercatopurine, dexamethasone, cyclophosphamide, soluble TNF receptors, antibodies, and humanized antibodies.

As used in the methods and compositions of the present disclosure, the term "pharmaceutically acceptable salts" refers to salts prepared from pharmaceutically acceptable non-toxic acids or bases including inorganic acids and bases and organic acids and bases. The sodium or di-sodium salts of aminopterin are pharmaceutically acceptable salts of aminopterin. As used herein, the term "aminopterin", unless specified otherwise, refers to the acid form of aminopterin or a pharmaceutically acceptable salt of aminopterin.

Since aminopterin is both basic and acidic, salts may be prepared from pharmaceutically acceptable non-toxic acids or bases including inorganic and organic acids or inorganic and organic bases. Such salts may contain any of the following anions: acetate, benzensulfonate, benzoate, camphorsulfonate, citrate, fumarate, gluconate, hydrobromide, hydrochloride, lactate, maleate, mandelate, mucate, nitrate, pamoate, phosphate, succinate, sulfate, tartrate and the like. Such salts may also contain the following cations: aluminum, calcium, lithium, magnesium, potassium, sodium, zinc, benzathine, chloroprocaine, choline, diethanolamine, ethylenediamine, meglumine, and procaine.

Unless the route of administration is specified in a method disclosed herein, any suitable route of administration may be employed for providing a human with a therapeutically effective amount of aminopterin, or a pharmaceutically acceptable salt thereof. For example, oral, intrathecal, rectal, parenteral, transdermal, subcutaneous, intramuscular, and the like may be employed as appropriate. Dosage forms include tablets, coated tablets, troches, dispersions, suspensions, solutions, caplets, capsules, patches, and, the like. Pharmaceutical compositions include those suitable for oral, rectal, intrathecal, and parenteral (including subcutaneous, intramuscular, and intravenous) administration, although the most suitable route in any given case will depend on the nature and severity of the inflammatory disorder being treated. The most preferred route of the present disclosure is the oral route. The pharmaceutical compositions may be conveniently presented in unit dosage form, and prepared by any of the methods well known in the art of pharmacy.

Pharmaceutical compositions of the present disclosure suitable for oral administration may be presented as discrete units such as capsules, cachets, or tablets, or aerosols sprays, each containing a predetermined amount of the pharmaceutically active ingredient, as a powder or granules, or as a solution or a suspension in an aqueous liquid, a non-aqueous liquid, an oil-in-water emulsion, or a water-in oil liquid emulsion. Such pharmaceutical compositions may be prepared by any of the methods of pharmacy, but all methods include the step of bringing into association the active pharmaceutical ingredient with at least one pharmaceutical carrier. In general, the pharmaceutical compositions are prepared by uniformly and intimately admixing the active pharmaceutical ingredient with liquid pharmaceutical carriers or finely divided solid pharmaceutical carriers or both, and then, if necessary, shaping the product into the desired presentation.

For example, a tablet may be prepared by compression or molding, optionally, with one or more accessory ingredients. Compressed tablets may be prepared by compressing in a suitable machine the active pharmaceutical ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 0.5 mg to about 2 mg of aminopterin or a therapeutically acceptable salt thereof, and each cachet or capsule contains from about 0.5 mg to about 2 mg of aminopterin or a therapeutically acceptable salt thereof. Most preferably, the tablet, cachet or capsule contains either one of two dosages, about 0.5 mg or about 1 mg of aminopterin or a therapeutically acceptable salt thereof.

In still other embodiments, pharmaceutical compositions contain a therapeutically effective amount of aminopterin, or a therapeutically acceptable salt thereof, with a standard deviation of less than 5%, and more preferably a standard deviation of less than 3%. The standard deviation is a measure of dose uniformity (i.e. consistency) in the pharmaceutical compositions with a smaller standard deviation being an indication of greater dose uniformity. The pharmaceutical compositions may be different portions of a single pharmaceutical composition from a single formulation batch, or may be from multiple pharmaceutical compositions of the same dosage form that are each the result of different formulation batches. Thus, the standard deviation can be a measure of dose uniformity both within the same batch and between batches.

The standard deviation of an antifolate in pharmaceutical compositions is determined by measuring the amount of antifolate in a known amount of each pharmaceutical composition using methods familiar to those in the art. For example, the amount of aminopterin and methotrexate in a pharmaceutical composition can be quantitated using scanning uv spectrophotometry, HPLC, or a radioligand DHFR binding assay [see Kamen et al., *Anal Biochem.* 70:54, 1976 and Ratliff et al., *J. Clin. One.* 16:1458, 1998]. As defined herein, calculation of a standard deviation requires measuring aminopterin from at least two randomly selected parts of a single batch of a pharmaceutical composition, or from each of at least two different batches of a pharmaceutical composition.

The disclosure is further defined by reference to the following examples describing in detail, the methods, and use and preparation of the pharmaceutical compositions. It will be apparent to those skilled in the art, that many modifications, both to materials, and methods, may be practiced without departing from the purpose and interest of the invention.

EXAMPLES

In Examples 1-15 that follow, "aminopterin" is the antifolate in an active pharmaceutical ingredient employed in a pharmaceutical composition substantially free of impurities.

Example 1

Efficacy in the Murine Air-Pouch Model of Inflammation

To identify the optimum dose of aminopterin for treating rheumatoid arthritis and to quantitate its potency relative to methotrexate, we tested aminopterin and methotrexate in a murine air-pouch model of inflammation whose dose-response relationship to methotrexate has been shown by Cronstein et al. to correlate exceedingly well with the dose-response relationship of methotrexate in humans [Cronstein, B. N., D. Naime, and E. Ostad, The anti-inflammatory mechanism of methotrexate. Increased adenosine release at inflamed sites diminishes leukocyte accumulation in an in vivo model of inflammation. *J. Clin. Invest.*, 1993. 92(6): 2675-82].

Accordingly, groups of 5 animals each (10-15 week-old male mice) were given a fixed dose (mg/kg) per group of aminopterin (0.0005, 0.001, 0.002, 0.005, 0.008, 0.010, 0.050) or methotrexate (0.01, 0.02, 0.05, 0.08, 0.10, 0.50, 1.00) by weekly ip injection on days 1, 7, 14 and 21. One readily recognizes that the above fixed doses for a 0.25 kg animal, for example, would represent 0.000125 mg, 0.00025 mg, 0.0005 mg, 0.00125 mg, 0.002 mg, 0.0025 mg, and 0.0125 mg aminopterin, respectfully, and 0.0025 mg, 0.005 mg, 0.0125 mg, 0.02 mg, 0.025 mg, 0.125 mg, and 0.25 mg methotrexate, respectfully. A separate group of 5 animals was given vehicle by ip injection on the same days (0.9% saline, control, n=5). On day 16, air pouches were induced on the animals by injecting 3 ml of air subcutaneously on the back. On day 22 (i.e. one day after the last dose of drug or vehicle), inflammation was induced by injection of 1 ml of a suspension of carrageenan (2% weight/volume in calcium- and magnesium-free PBS). The mice were put back in their cages and allowed to run free for 4 hours. The mice exhibited no signs of toxicity at the end of the dosing period. After 4 hours, the animals were sacrificed, the pouches flushed with 2 ml of PBS and the exudates harvested. Aliquots were diluted 1:1 with methylene blue (0.01% w/v in PBS), and the cells were counted.

These studies demonstrated that aminopterin and methotrexate diminished in a dose-dependent fashion the number of neutrophils that accumulated in the carrageenan-treated air pouches with $EC_{50}$s of 0.0009 mg/kg/wk and 0.04 mg/kg/wk, respectively (FIG. 1). Thus, aminopterin was found to be 43-fold more potent than methotrexate (P<0.001). That efficacy of aminopterin can be obtained at such low weekly doses has not been reported in the prior art. Weekly doses in the above range are known to be many-fold below the maximally tolerated weekly dose of aminopterin, where mucositis just starts to appear [Ratliff, et al., Phase I and pharmacokinetic trial of aminopterin in patients with refractory malignancies. *J. Clin. Oncol.*, 1998. 16(4): 1458-64].

Example 2

Duration of Efficacy in The Murine Air-Pouch Model of Inflammation

Figure 2:
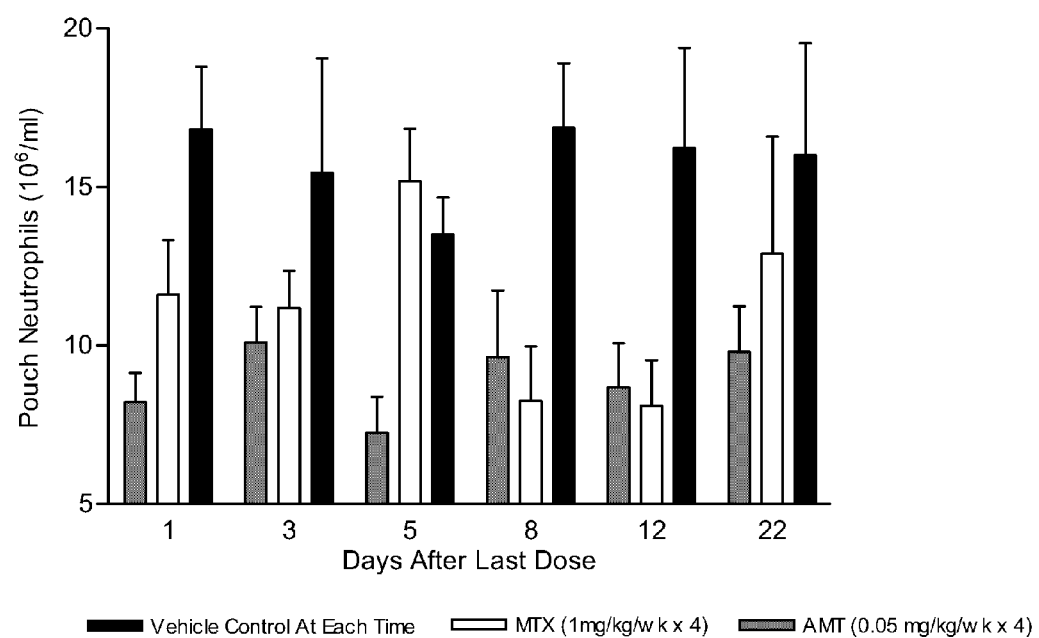
FIG. 2 is a plot showing the efficacy of aminopterin and methotrexate days after the last dose of each drug in the murine air-pouch model of human inflammation.

Although the 43-fold difference in $EC_{50}$s between aminopterin and methotrexate in their anti-inflammatory activity was felt to be most likely due to the preferential uptake efficiency of aminopterin, we also considered the possibility that a difference in the rate of drug excretion from cells could be contributing to this difference by essentially increasing the magnitude of the "trough" of one drug over another prior to each weekly dose. We therefore examined the rate at which anti-inflammatory activity was lost in the air-pouch model after the cessation of 4 weeks of dosing at the maximally efficacious dose (FIG. 2).

Accordingly, animals (10-15 week-old male mice) were given weekly ip injections of vehicle (0.9% saline, control, n=60), aminopterin (n=60, 0.05 mg/kg) or methotrexate (n=60, 1.0 mg/kg) over the course of a month on days 1, 7, 14 and 21. On day 16, air pouches were induced on the animals by injecting 3 ml of air subcutaneously on the back. On day 25 the air pouches were re-inflated with 1.5 ml of air. Pouches were re-inflated as needed to maintain them. On days 22 (+1), 24 (+3), 26 (+5), 29 (+8), 33 (+12), and 43 (+22) inflammation was induced in a group of n=5 animals from the vehicle, aminopterin and methotrexate arms of the study by injection of 1 ml of a suspension of carrageenan as a 2% weight/volume solution in calcium-free and magnesium-free PBS (numbers in parentheses indicate days after the fourth and last ip injection of either vehicle or drug). After 4 hours, the mice were sacrificed, the pouches flushed with 2 ml of PBS and the exudates harvested. Aliquots were diluted 1:1 with methylene blue (0.01% w/v in PBS), and the cells were counted.

The data showed no statistically significant difference between the rate of recovery of inflammation at 8, 12 or 22 days after the last antifolate dose, and revealed that the duration of action of both aminopterin and methotrexate was quite long, consistent with the long intracellular half-lives of polyglutamated antifolates. This example shows that the greatest duration between the last dose of one cycle and the first dose of the next cycle can be up to 21 days for aminopterin.

Example 3

Efficacy in the Rat Oxygen-Toxicity Model of Inflammation

To identify the optimum dose of aminopterin for treating bronchopulmonary dysplasia in humans and to quantitate its potency relative to methotrexate, we tested aminopterin and methotrexate in a murine oxygen-toxicity model of inflammation [Deng, H.; Mason, S, N.; Richard L. Auten, J. Lung inflammation in hyperoxia can be prevented by antichemokine treatment in newborn rats. *American Journal of Respiratory Critical Care Medicine* 2000, 162, 2316-2323].

Figure 3:
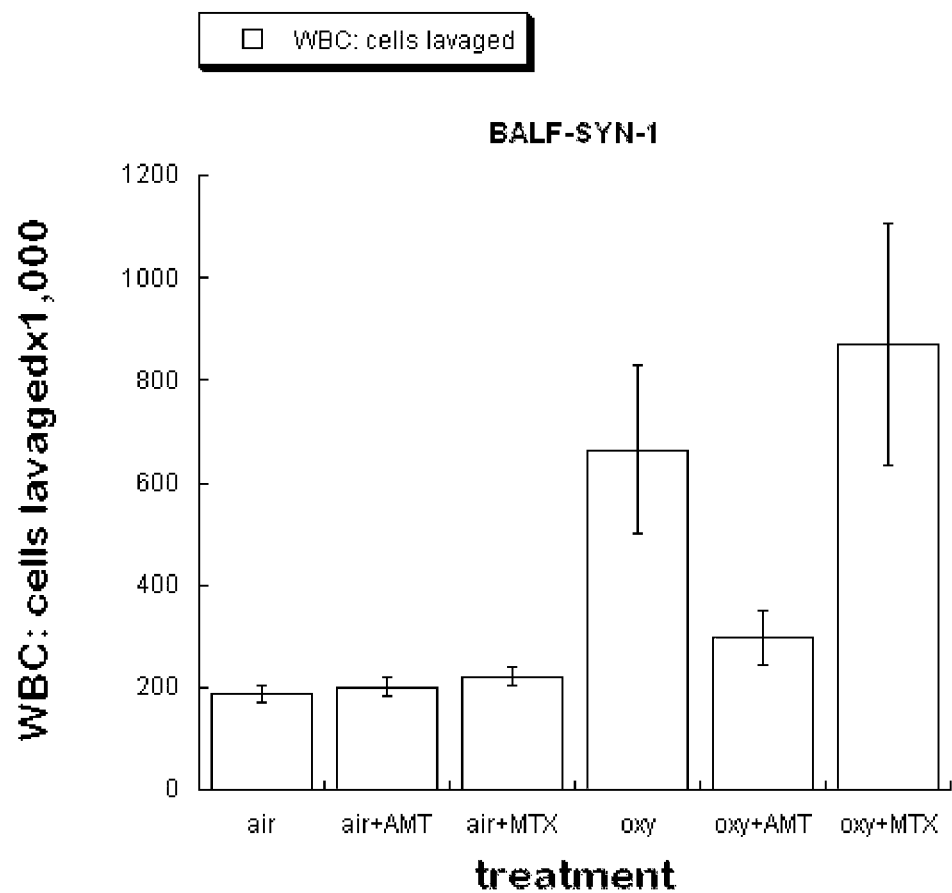
FIG. 3 is a plot showing the relative efficacy of aminopterin and methotrexate in the rat oxygen-toxicity model of human bronchopulmonary dysplasia.

Briefly, timed pregnant rats were placed in air (two litters) or 95% oxygen (one litter) the day of delivery after recombining litters among four just delivered dams. Litter sizes were the same. Aminopterin (0.2 mg/kg), methotrexate (0.35 mg/kg) or vehicle were then introduced by the ip route on day 2 after birth. Dams were rotated daily between air and oxygen cages to avoid maternal oxygen toxicity. On day 8, the pups were weighed and then euthanized, tracheas are cannulated and the pulmonary artery is perfused with saline. Bronchoalveolar lavage fluid (BALF) was then obtained for cell count and chemokine analysis (FIG. 3). The lungs were removed and snap frozen for myeloperoxidase activity assay (neutrophil accumulation within lung parenchyma) and 8-isoprostane, a marker of lipid oxidation. The pulmonary artery was perfused and the lungs were inflation-fixed with buffered formalin at 25 cm $H_2O$.

As expected, the data showed that hyperoxia resulted in a marked influx of inflammatory cells, predominantly comprised of neutrophils (PMNs). The data showed a statistically significant reduction in the number of neutrophils after only a single 0.2 mg/kg injection of aminopterin 6 days prior to sacrificing the animals. In contrast, methotrexate at 17-times the dose of aminopterin (0.35 mg/kg), failed to reduce the influx of neutrophils. Efficacy of aminopterin can be obtained using a single low dose. This example shows that bronchopulmonary dysplasia can be treated with an antifolate, and that achieving efficacy occurs at a much more rapid rate for aminopterin than for methotrexate. This dose is many-fold lower than the maximally tolerated dose of aminopterin, which produces mucositis [Ratliff, et al., Phase I and pharmacokinetic trial of aminopterin in patients with refractory malignancies. *J. Clin. Oncol.*, 1998. 16(4): 1458-64].

Example 4

2,4-Diamino-6-pteridinemethanol (5) hydrobromide Salt 2,4,5,6-Tetraminopyrimidine.$H_2SO_4$.$H_2O$ (75.0 g, 0.293 mole) was added to a stirred solution of $BaCl_2$.$2H_2O$ (71.5 g, 0.293 mole) in $H_2O$ (1.45 l.) at 85-90° C. The mixture was stirred rapidly at about 90° C. for 15 min, cooled to 40° C., and filtered from $BaSO_4$, which was washed thoroughly on a funnel with $H_2O$. The clear, yellow filtrate was then diluted further with $H_2O$ to give a volume of 4.35 l. This solution of the tetraminopyrimidine.2HCl was then added to a solution of NaOAc (4.35 l. of 4 N) in which dihydroxyacetone (79.3 g, 0.88 mole) and cysteine.HCl.$H_2O$ (51.5 g, 0.293 mole) had just been dissolved. The resulting solution was stirred mechanically at room temperature while a slow stream of air was continuously passed through it for 26 hr. (Yellow-orange solid began separating after 2 hr.) The mixture was then kept in a refrigerator for 16 hr before the solid was collected, washed successively with cold $H_2O$, EtOH, and $Et_2O$ before it was dried to constant weight in vacuo over $P_2O_5$ at 25° C. [The crude product mixture (47 g) was weighed in order to obtain an estimate of the volume of 48% HBr required to form hydrobromide salts.] A mechanically stirred mixture of the dried solid and EtOH (6.05 l.) was heated to 70° C., and a solution of 48% HBr (28 ml) in EtOH (490 ml) was added in a thin stream while the mixture was maintained at 70-75° C. The mixture was then refluxed for about 5 min with rapid stirring while nearly all of the solid was dissolved. The hot solution was treated with Norit and filtered through a Celite mat. The clear yellow filtrate was kept in a refrigerator overnight while a first crop of orange-colored solid separated. The collected solid was washed with EtOH, then dried in vacuo (56° C. over $P_2O_5$) to give 17.2 g of product. The filtrate was concentrated by evaporation (rotary evaporator, $H_2O$ aspirator, bath to 35° C.) to about 2 l. and then refrigerated to give a second crop, which was dried as before, of 10.2 g; total yield 27.4 g (34%). The $^1$H NMR spectrum of this material in $CF_3CO_2D$ showed it to contain a barely detectable amount of methyl substituted 2,4-diaminopteridine.HBr as evidenced by very weak signals at $\delta2.83$ ($CH_3$) and $\delta8.85$ (pteridine ring H). Strong signals produced by the desired product occur at $\delta5.28$ (6-$CH_2O$) and $\delta9.08$ ($C_7$—H). The proportion of desired product to the methyl-substituted contaminant was estimated from the $^1$H NMR integrals to be 20:1. The $^1$H NMR spectrum also revealed retention of a small amount of EtOH in the product dried as described but not enough to interfere with the conversion of it to 2.

Example 5

2,4-Diamino-6-(bromomethyl)pteridine (2) hydrobromide salt from (5)

Bromine (59.6 g, 0.373 mole) was added dropwise over a 30-min period to a stirred solution of triphenylphosphine (97.7 g, 0.373 mole) in anhydrous 486 ml of dimethylacetamide (DMAC) kept at about 10° C. (ice bath) and protected from atmospheric moisture. (Bromine remaining in the funnel was rinsed with 10 ml of DMAC). A smooth suspension containing finely divided, crystalline triphenylphosphine dibromide resulted. The 2,4-diamino-6-pteridinemethanol-.HBr (2) (25.4 g, 0.093 mole) described above was added in one portion through a powder funnel (with the aid of 10 ml DMAC). The ice bath was removed, and the stirred mixture was allowed to warm to 20-25° C. After about 1 hr, complete solution had occurred. The solution, which gradually developed a dark-red color, was kept at 20-25° C. for 1 hr longer and was then chilled (ice bath) before it was treated with EtOH (72 ml). After overnight refrigeration, the solvents were removed by evaporation in vacuo. The dark, semisolid residue was stirred with two 300-ml portions of benzene (to remove triphenylphosphine oxide), and each portion was removed from the benzene-insoluble product by decantation. The solid that remained was dissolved with stirring in glacial AcOH (660 ml) which had been preheated to 80° C. The mixture was kept in a bath at 80° C. until solution was complete. A tan crystalline solid separated as the dark solution was allowed to cool. Overnight refrigeration caused the AcOH to partially freeze. When it had thawed, the solid was collected, washed with chilled AcOH followed by $Et_2O$, and dried in vacuo (over $P_2O_5$ and NaOH pellets) at successive temperatures of 25° C., 56° C., and 110° C. (The higher temperature was necessary for complete removal of AcOH). The yield was 15.3 g (49%). (Some runs afforded 60% yield). This sample was further purified by reprecipitation from MeOH solution (Norit) by addition of $Et_2O$ followed by drying in vacuo (25° C., $P_2O_5$), yield 13.0 g (42%) of pale-yellow solid. Spectral data: $\lambda$max, nm ($\epsilon\times10^{-3}$), 0.1 N HCl, 249 (17.3), 339 (10.5), 353 (sh); pH 7, 258 (21.2), 370 (6.87); 0.1 N NaOH, 258 (21.5), 370 (6.94); $^1$H NMR($CF_3CO_2D$), $\delta$ 4.70 (s, 2, $CH_2$) and $\delta$ 9.08 (s, 1, $C_7$—H); estimated proportion relative to the methyl-substituted contaminant, 25:1. The preparation of 2 described above is typical of several runs that gave similar yields of material whose $^1$H NMR spectra differed only slightly in the estimated proportion of 2 with respect to the methyl-substituted contaminant. The proportions usually ranged from 16:1 to 25:1, which corresponds to a percentage of 2 of 94 to 96%.

Example 6

2,4-Diamino-6-(bromomethyl)pteridine (2) hydrobromide salt from (1)

A suspension of 5 mmol 2,4,5,6-tetraminopyrimidine dibromide in 50 ml methanol was treated with a solution of 7.5 mmol β-bromopyruvaldoxime in 10 ml of methanol at reflux temperature for 2 h. The 2,4-diamino-6-(bromomethyl)pteridine was collected after neutralization with concentrated $NH_3$ at room temperature, washed with methanol, ether and dried at 100° C. in an oven. $^1$H NMR (250 MHz, ppm, DMSO-$d_6$), $\delta$ 8.84 (s, 1H, $C_7$—H). The yield was 88%.

Example 7

Active Pharmaceutical Ingredient Containing Aminopterin (4)

A mixture of 2 (168 mg, 0.500 mmole) and N-(4-aminobenzoyl)-L-glutamic acid, compound 3 (400 mg, 1.50 mmoles) in DMAC (2 ml) was stirred at 25° C. under $N_2$ in a stoppered flask protected from light. Solution occurred after 2 hrs. After 18 hrs, the orange solution was mixed with $H_2O$ (15 ml) with stirring to give a finely divided, yellow precipitate. The mixture was centrifuged, and the supernatant removed by decantation. The yellow solid was stirred with four 15-ml portions of $H_2O$, each of which was removed by decantation after centrifugation. The solid was then suspended in EtOH (15-20 ml), collected by filtration, washed with $Et_2O$, and dried in vacuo (25° C., $P_2O_5$) to give hydrated 4 in 68% yield (160 mg). Anal. Calcd for $C_{19}H_{20}N_8O_5 1.75H_2O$: C, 48.36; H, 5.02; N, 23.74. Found: C, 48.72; H, 4.91; N, 23.36. Spectral data: $\lambda$max, nm ($\epsilon\times10^{-3}$), 0.1 N HCl, 244 (18.2), 290 (20.5), 335 (11.0); pH 7, 260 (26.7), 283 (25.5), 370 (8.00); 0.1 N NaOH, 260 (26.9), 283 (25.3), 370 (8.00); $^1$H NMR (DMSO-$d_6$), $\delta$2.02 (m, 2, $CHCH_2CH_2$), 2.32 (m, 2, $CH_2CO_2H$), 4.36 (m, 1, $NHCHCO_2H$), 4.52 (s, 2, $CH_2N$), 6.85 (m, 4, 2 phenylene protons plus $NH_2$), 7.72 (m, 2, phenylene), 7.86 (broad s, 2, $NH_2$), 8.13 (d, 1, NHCO), 8.72 (s, 1, $C_7$—H). Examination by tlc revealed one uv-absorbing spot and no fluorescence at any point. The product may be used directly as the active pharmaceutical ingredient, but is occasionally subjected to one or more re-crystallizations from water or formamide to improve the aminopterin purity slightly. The active pharmaceutical ingredient is stored in the presence of desiccant.

Examples 8-13

Analysis of Active Pharmaceutical Ingredient

Three different 1 mM solutions of a first batch of the active pharmaceutical ingredient prepared according to Example 59 were prepared by weighing out 2.3 mg, 4.5 mg and 1.8 mg of the active pharmaceutical ingredient as if it were 100% aminopterin (FW 440.42 g/mole), and dissolving it into 5.223 ml, 10.218 ml, and 4.087 ml of 0.001 N NaOH, respectively. Twenty μl of each 1 mM solution was subjected to HPLC analysis by injecting each onto a C18 column (Waters μBondapak 125 Å, 10 μm, 3.9×150 mm) using an isocratic mobile phase consisting of 5 mM PicA, 10 mM $NH_4H_2PO_4$ and 20% methanol at a pH of 6.8. The flow rate of the mobile phase was 1 ml/min, and the analysis was performed at room temperature. Using a Waters 996 PDA UV spectrophotometer, absorbance data from 210 nm to 400 nm was captured. The data was analyzed with the Waters Millennium software by extracting the chromatogram at 282 nm and calculating the peak area percentages. The data was also analyzed by extracting the spectra of individual peaks, allowing the identification of pABAGlu, folic acid, aminopterin and pterin species by their characteristic spectra.

The average of the HPLC analyses of the three separate 1 mM solutions revealed that the first batch of active pharmaceutical ingredient consisted of approximately 96.27 area % aminopterin and 3.73 area % impurities, wherein the impurities were made up of 0.23 area % folic acid, 2.18 area % N-(4-aminobenzoyl)-L-glutamic acid (i.e. pABAGlu), and 0.92 area % of a pterin, probably 2,4-Diamino-6-(bromomethyl)pteridine, and 0.4 area % of at least two other unidentified impurities (Example 8, Table 1). A similar HPLC analysis revealed that a second batch of active pharmaceutical ingredient consisted of 97.23 area % aminopterin and 2.775 area % impurities, wherein the impurities were made up of 1.82 area % folic acid, 0.556 area % N-(4-aminobenzoyl)-L-glutamic acid (i.e. pABAGlu), 0.343 area % pterin, probably 2,4-diamino-6-(bromomethyl)pteridine), and 0.056 area % of an unidentified impurity (Example 9, Table 1). By comparison, the prior art active pharmaceutical ingredients contained aminopterin and variable amounts of impurities ranging up to 41% (Examples 10-13, Table 1).

TABLE I

| Example | AMT purity | AMT total impurities | Composition of total impurities |
|---|---|---|---|
| 8 | 96.27% | 3.730% | FA (0.23%); pABAGlu (2.18%); pterins (0.92%); other (0.4%) |
| 9 | 97.23% | 2.775% | FA (1.82%); pABAGlu (0.556%); pterins (0.343%); other (0.056%) |
| 10*,a | 70-80% | 20-30% | not specified |
| 11*,b | <80% | >20% | FA (20%); others unspecified |
| 12*,c | 80% | 20% | FA (15%); pterins (5%) |
| 13*,d | 59% | 41% | not specified |

Percentages are HPLC peak areas.
Abbreviations: FA, folic acid; AMT, aminopterin; and pABAGlu, N-(4-aminobenzoyl)-L-glutamic acid.
*Not part of the subject invention.
[a]Seeger, et al., J. Am. Chem. Soc. 71: 1753, 1949.
[b]Heinrich et al., J. Am. Chem. Soc. 75: 5425.
[c]Loo, J. Med. Chem. 8: 139, 1965.
[d]Sirotnak and Donsbach, Biochem. Pharmacol. 24: 156, 1975.

Example 14

Pharmaceutical Compositions

This example illustrates the preparation of pharmaceutical compositions substantially free of impurities. As used in this example, "API" means an active pharmaceutical ingredient substantially free of impurities, wherein the antifolate in the API is aminopterin, or a pharmaceutically acceptable salt thereof. The aminopterin purity of the API is used to establish how much API is required in the pharmaceutical composition to obtained a desired final amount of aminopterin, or a pharmaceutically acceptable salt thereof, in the pharmaceutical composition.

Tablets: Surface deposit aminopterin by combining 16.8 grams API, 791.0 grams microcrystalline cellulose, 553.7 grams lactose monohydrate, 1.5 g NaOH and 632 grams of sterile water. Mix and dry overnight. Add 1311 grams of this surface deposited aminopterin to 171 grams of lactose, 3.9 grams colloidal silicon dioxide, 46.2 grams sodium croscarmellose, and 7.7 grams magnesium stearate to provide a total weight 1540 grams. Compress into approximately 15,000 tablets using a tableting machine, wherein each tablet weighs approximately 100 mg and contains about 1 mg aminopterin.

Gelatin capsules: Prepare by mixing 0.5 grams of API with 0.5 grams magnesium stearate, and 99 grams of lactose. Dispense 100 mg of this mixture into hard-shell gelatin capsules to provide each capsule with about 0.5 mg of aminopterin.

Suspension: An aqueous suspension is prepared for oral administration so that each 5 ml contains about 2 mg aminopterin by mixing 40 mg of API with 20 grams of sodium carboxymethyl cellulose, 0.5 grams of sodium benzoate, 100 grams of sorbitol solution U.S.P., and 2.5 ml of vanillin.

Liquid for injection or oral administration: Clean glassware to be used with 2 M NaOH for 3-5 minutes and the rinse thoroughly with deionized water. Prepare a first saline buffer by adding 2.7017 grams of dibasic sodium phosphate, USP to 5 liters of 0.9% sodium chloride for injection, USP. Prepare a second saline buffer by adding 1.39 grams of monobasic sodium phosphate, USP to 1 liter of 0.9% sodium chloride for injection, USP. While stirring the first saline buffer solution, slowly add the second saline buffer solution until the final pH is 7.9-8.1. Record the final volume. Add sufficient API to provide 0.4 mg/ml aminopterin (i.e. 2 mg aminopterin per 5 ml) and filter through a 0.2 micron membrane filter and package under sterile conditions in 10-ml vials each containing 5 ml. Use within 2 months.

Injectable: A parenteral formulation is prepared by mixing 0.200 grams of API with 20.0 grams of propylene glycol, 20.0 grams of polyethylene glycol 400, and 1.0 gram of polysorbate 80. A sufficient quantity of 0.9% saline solution is then added with stirring to provide 100 ml of solution which is filtered through a 0.2 micron membrane filter and packaged under sterile conditions in 2-ml vials each containing 1 ml, or a total of about 2 mg/vial aminopterin. The solution is diluted 10-fold with 0.9% saline solution prior to administration via an intravenous route.

Example 15

Mean and Standard Deviation of Dose in Pharmaceutical Compositions

The average dose and the dose uniformity (i.e. standard deviation) of aminopterin among 10 randomly selected tablets were determined for a batch of 15,000 1 mg aminopterin tablets prepared according to Example 14 (Table II). The mean dose and dose uniformity were obtained by scanning spectrophotometry and a radioligand binding assay using dihydrofolate reductase (DHFR) as binder and methotrexate as a standard.

TABLE II

| Random Tablet | aminopterin dose by spectrophotometry (mg) | aminopterin dose by radioligand binding assay (mg) |
|---|---|---|
| 1 | 0.99 | 1.03 |
| 2 | 0.98 | 0.93 |
| 3 | 0.99 | 1.04 |
| 4 | 0.97 | 1.04 |
| 5 | 0.94 | 0.96 |
| 6 | 0.96 | 1.05 |
| 7 | 0.99 | 0.99 |
| 8 | 0.94 | 1.03 |
| 9 | 0.97 | 1.01 |
| 10 | 1.01 | 1.03 |
| mean | 0.974 | 1.01 |
| standard deviation | 2.271% | 3.929% |

For scanning spectrophotometry, each of ten tablets are dissolved in 11.35 ml of water by rotating in a 15 ml tube for 30 minutes at room temperature to make an approximately 200 µM solution (i.e. about 1 mg aminopterin with a FW of 440 g/mole in 11.35 ml). The tubes are spun, and a portion of the supernatant is diluted ten-fold with 0.1 N NaOH to a final concentration of 20 µM. The absorbance of the diluted supernatant is read at 282 nm and 260 nm on a Perkin-Elmer Lambda 4B scanning spectrophotometer (1 cm path length) and the concentration of the diluted sample calculated using the relationships, concentration (in µM) at 282 nm=10×($OD_{282}/0.264$) and concentration (in µM) at 260 nm=10×($OD_{260}/0.285$). The mg/ml at 282 nm and 260 nm is then calculated using the relationship, mg/ml=concentration (in µM)×0.00044. The total mg of aminopterin in each tablet is then determined by multiplying the mg/ml determined at 282 nm and 260 nm by 113.5. The mg of aminopterin per tablet is then reported as the average of the mg of aminopterin in each tablet determined at 282 nm and 260 nm. For example, using the above procedure, a 1 mg aminopterin tablet yields an $OD_{282}$ of 0.5227, and a calculated concentration (in µM), mg/ml, and total mg of aminopterin of 19.8 µM, 0.008712 mg/ml, and 0.9888 mg, respectively. Using the above procedure, the same 1 mg aminopterin tablet yields an $OD_{260}$ of 0.5641, and a calculated concentration (in µM), mg/ml, and total mg of aminopterin of 19.8 µM, 0.008712 mg/ml, and 0.9888 mg, respectively. The reported amount of aminopterin in the tablet is the mean of total aminopterin in the tablet calculated at 282 nm and 260 nm, or 0.9888 mg.

The radioligand binding assay was performed essentially as described previously for methotrexate [see Kamen et al., Anal. Biochem. 70:54, 1976 and Ratliff et al., J. Clin. Onc. 16:1458, 1998]. Briefly, a standard curve was developed for 0.2 to 1.0 pmol methotrexate binding to partially purified chicken liver DHFR, wherein binding of a known amount of non-radioactive methotrexate results in the displacement of an amount of tritiated methotrexate (i.e. radioactive $^{3}$H-methotrexate). Aminopterin and methotrexate are equivalent in the assay in terms of their displacement and binding, and the absolute detection limit of the assay is 0.05 to 0.10 pmol of antifolate. After the standard curve is established, a portion of the 200 µM supernatant prepared above for an aminopterin tablet is further diluted 10,000 using two serial 100-fold dilutions with water to provide an approximately 20 nM solution of aminopterin. The DHFR assay is performed with 100 µL of the 20 nM solution, as well as several 2-fold serial dilutions, and the result expressed as pmol/ml aminopterin. The total number of pmol of aminopterin is calculated using the relationship, pmol/ml×10,000×11.35. The total number of mg in the tablet is then calculated using the relationship, total pmol×($10^{-6}$ µmole/pmol)×0.44 mg/µmole.

As determined by scanning spectrophotometry, the average dose and the dose uniformity (i.e. standard deviation) of aminopterin among 10 randomly selected tablets from a batch of 15,000 1 mg aminopterin tablets was 0.974 mg and 2.271%, respectively (Table II). As determined by radioligand binding assay, the average dose and the dose uniformity (i.e. standard deviation) of aminopterin among the same 10 tablets was 1.01 mg and 3.929%, respectively (Table II).

Example 16

Animal Model of Multiple Sclerosis

Using the rat EAE animal model of multiple sclerosis, a series of prophetic studies are performed wherein aminopterin is given to animals using both active and passive protocols for inducing EAE (Burton, Agents and Actions (1989) 27 (3/4): 351-355). In the active protocol, animals are intradermally injected with myelin basic protein (MBP), Freund's adjuvant and mycobacteria, whereas in the passive protocol separate donor rats are immunized actively and then 10-12 days after active immunization, donor splenocytes are collected and stimulated in vivo with MBP for 3 days, then $1-2\times10^{8}$ leukocytes injected iv into each irradiated (600 rads) recipient rat. Aminopterin at doses of 0.0005, 0.001, 0.002, 0.005, 0.008, 0.010, 0.050, 0.1 and 0.5 mg/kg are administered ip on the day after active or passive sensitization. One or more of the doses of aminopterin inhibits the onset of active EAE by greater than 80% and passive EAE by greater than 80%. The inhibition will persist for up to 14 days after the single dose, whereas in untreated controls actively stimulated EAE begins on day 7 and continues for 20 days before beginning to reverse, and in passively stimulated EAE symptoms begin on day 5 and begin to reverse on day 12. Animals will show a clear dose-response over the range of aminopterin doses whether sensitized actively or passively.

Example 17

Human Multiple Sclerosis

A prophetic randomized, double-blinded, placebo-controlled, clinical trial of low-dose, weekly, oral aminopterin is performed in 60 patients with clinically definite chronic progressive multiple sclerosis (MS) attending a referral-based outpatient MS clinic. Study patients are 21 to 60 years old with a disease duration of longer than 1 year. Patients' Expanded Disability Status Scale scores were 3.0 to 6.5 (ambulatory with moderate disability). Patients are first stratified by Expanded Disability Status Scale scores, 3.0 to 5.5 and 6.0 to 6.5, and then were randomized to receive aminopterin or placebo treatment. Treatment consists of weekly, oral, low-dose (1.0-2.0 mg) aminopterin or placebo for 2 years, followed by observation for as long as 1 year. A composite outcome measurement instrument is used and consists of (1) Expanded Disability Status Scale (EDSS), (2) ambulation index, (3) Box and Block Test, and (4) 9-Hole Peg Test. Failure of therapy is indicated by a designated change that is sustained for more than 2 months in one or more components of this composite measure. Significantly less progression of impairment is measured by one or more validated tests of EDSS, ambulation index, Box and Block Test, 9-Hole Peg Test, upper-extremity function or a composite score thereof in the aminopterin treatment group in the absence of clinically significant toxicity. The change in T2-weighted total lesion area (T2W-TLA) is significantly related to sustained change in performance in one or more of the above validated tests.

Example 18

Canine Atopic Dermatitis Treated with Aminopterin

The efficacy of aminopterin in the treatment of canine atopic dermatitis (CAD) was demonstrated in a 4-week open-label trial followed by an optional one year extension. Five dogs were treated orally with 0.01 mg/kg/week of aminopterin, except for one subject whose dose was escalated to 0.015 mg/kg/week at week 4. Subjects were assessed at baseline and at weeks 2 and 4 of the trial, and every other week of the 1-year extension phase. Outcome measures included (1) investigator grading of lesions using the Canine Atopic Dermatitis Extent and Severity Index (CADESI, a composite index used in the approval of cyclosporine for CAD), (2) owner assessment of pruritis using a Pruritis Visual Analog Scale (PVAS); and overall assessment of efficacy by investigators and owners categorized as no (<10%), poor (10-25%), fair (25-50%), good (50-75%), very good (75-90%) and excellent (>90%) efficacy.

All 5 dogs completed the original 4 week segment of the pilot trial, where the median improvements (range) from baseline in outcome measures were: CADESI score=−59% (−11 to −91%); PVAS score=−4 (−4 to +2); composite CADESI×pruritis score=−60% (−97 to +24%); overall evaluation of efficacy by clinicians=2 (fair (1 to 5); and overall evaluation of efficacy by owners=2 (fair)(1 to 4). Importantly, there has been no clinical evidence of hematologic (CBC) or liver toxicity (LFTs) observed in the dogs treated for CAD at up to 20 weeks at 0.01 mg/kg/week, a dose equivalent to 0.7 mg/week in a 70-kg human.

Figure 4:
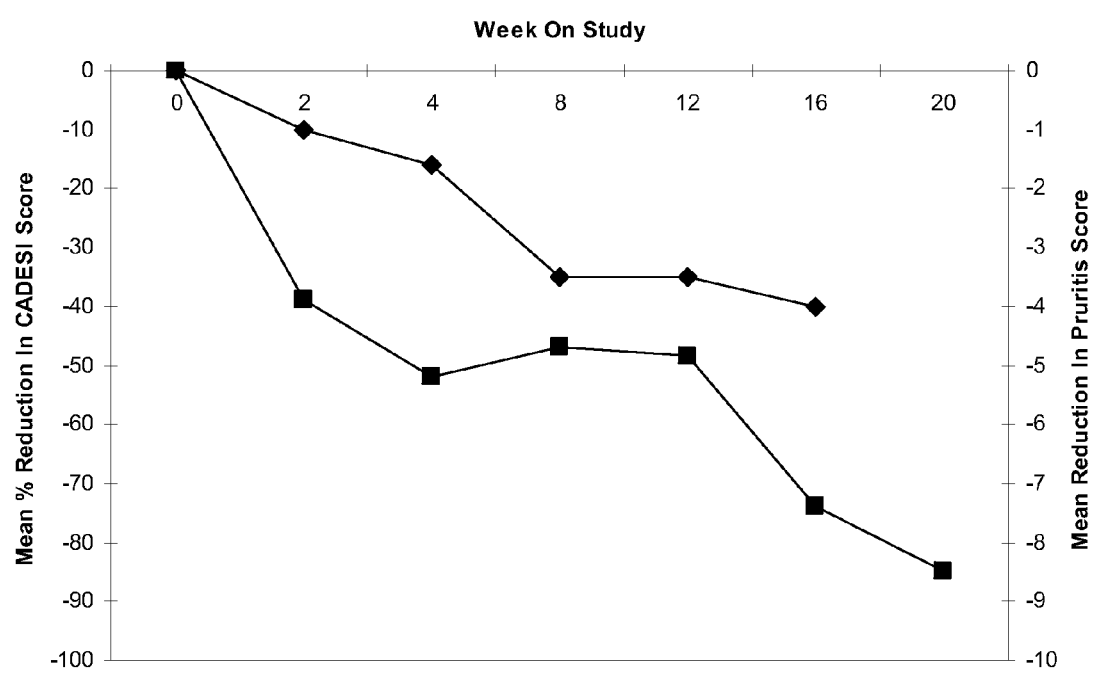
FIG. 4 is a plot showing the efficacy of aminopterin in canine atopic dermatitis in a 4-week trial.

The reduction in the mean percent CADESI and pruritis PVAS scores during the pilot and extension phases are graphically depicted for the subjects remaining enrolled at each week of the study (FIG. 4). During the extension phase, 3 dogs were withdrawn at various times for: unrelated medical reasons (1), increase in pruritis (1) and lack of compliance with drug administration (1). One dog appeared to be in near or complete remission. One dog had signs that failed to respond to aminopterin in the first phase, dosage was increased at week 4 and prednisone was added for 2 weeks for humane reasons. In total, prednisone was used intermittently in 3 dogs for humane considerations, antihistamines were used in 2 dogs without benefit in 1, and antibiotics were used in 1 dog.

Example 19

Canine Atopic Dermatitis Treated with Methotrexate

The efficacy of methotrexate in the treatment of CAD was demonstrated in a 4-week open-label trial. Five dogs were treated orally with about 0.2 mg/kg/week of methotrexate. Subjects were assessed at baseline and at weeks 2 and 4. Three dogs did not do well, one had not improved as of the last assessment and one dog improved markedly. It was observed that methotrexate took longer to produce efficacy compared to aminopterin.

Example 20

Adenosine Release by Aminopterin

Figure 5:
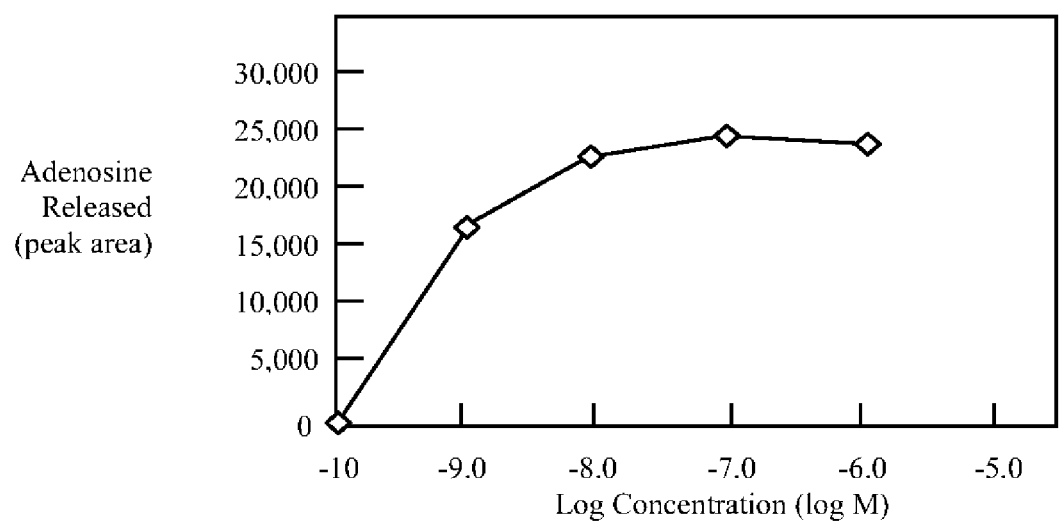
FIG. 5 is a plot showing adenosine release from ma104 cells after 8 hours incubation with various concentrations of aminopterin.

Various concentrations of aminopterin were incubated with ma104 cells for 8 hours, and the release of adenosine measured (FIG. 5). Aminopterin caused a dose-dependent release of adenosine with an $EC_{50}$ of 0.5 nM. The prior art shows the $EC_{50}$ of methotrexate to be approximately 1 nM (Cronstein'91).

Example 21

DHFR and MTX Binding in Liver

Figure 6:
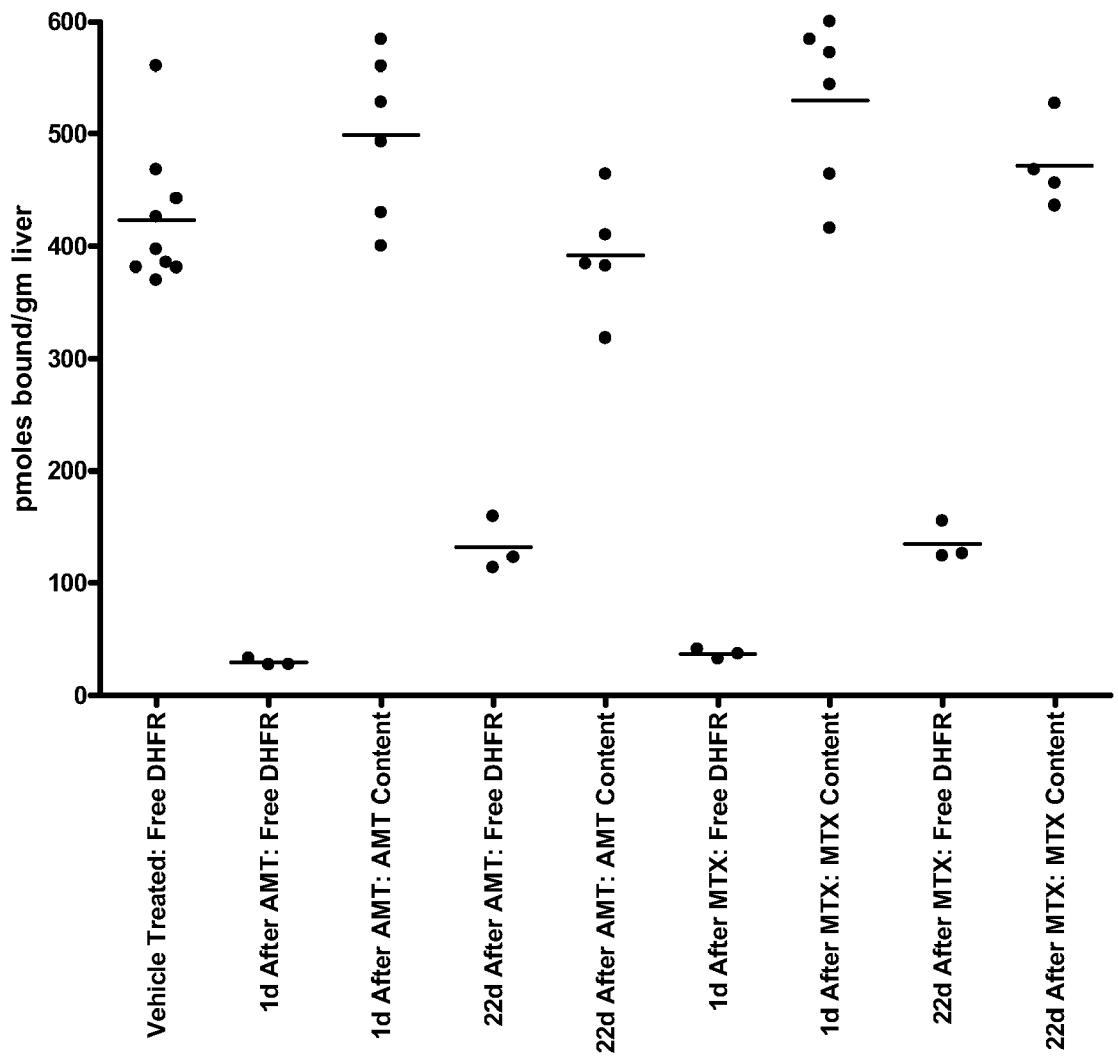
FIG. 6 is a plot showing the total amount of (aminopterin) AMT and methotrexate (MTX) in the liver after the cessation of dosing together with the amount of free dihydrofolate (DHFR).

The animals that were treated in Example 1 were further analyzed with respect to the free dihydrofolate reductase (DHFR) available in their livers (i.e., amount of DHFR unbound, or not inhibited by either AMT or MTX) (FIG. 6). The following procedure was used. Portions of frozen liver were weighed and homogenized in three volumes of assay buffer (10 mM $KPO_4$, 150 mM KCl, 1 mg/ml charcoal-treated BSA, 0.1 mg/ml NADPH, pH 7.5) on ice. After centrifugation for 30 min at 16000×G at 4° C., tissue extract was assayed for free DHFR by binding of 3H-MTX. Three serial 1:2 dilutions were made in assay buffer (total 100 µl/tube), starting with 10 µl extract for control samples (+190 µl buffer) or 100 µl for antifolate-treated samples. Approximately 2 pmoles of 3H-MTX (~100,000 dpms) in 100 µl buffer was added to each tube and mixed by addition of another 100 µl buffer and agitation. After 30 mins on ice, unbound 3H-MTX was removed by addition of 200 µl dextran-coated activated charcoal (2.5% activated charcoal and 0.5% dextran MW 10,000) and centrifugation. Radioactivity in the supernatant (=bound 3H-MTX) was counted after careful removal from the charcoal pellet and addition of Ultima Gold scintillation fluid. A charcoal "blank" consisting of buffer, 3H-MTX and charcoal was subtracted from each value. Results were calculated by averaging the dpms bound/100 µl of the three dilutions, converting to picomoles MTX (specific activity 49,000 dpms/picomole, determined by competitive radioligand assay), and multiplying by 30 to give picomoles/gm tissue.

The total amount of AMT and MTX in the liver at the indicated days after the cessation of dosing is plotted together with the amount of free DHFR as measured using the method described above (FIG. 6). The drug content data is reproduced from Example 1. This example shows that at the indicated weekly dosing frequency, AMT binds (i.e., inhibits) about 95% of the available DHFR in the liver 1 day (d) after the last of 4 sequential weekly doses; at 8 d after the last dose about 83% of the available DHFR has been inhibited; and that at 22 d after this last dose about 70% of the available DHFR has been inhibited. The amount of free (uninhibited) DHFR has increased via either loss of bound AMT and/or synthesis of new DHFR. The amount of AMT remaining in the tissue at 22 d after the cessation of dosing exhibits a reciprocal decrease to the increased amount of free DHFR. A substantially similar pattern of events happens in a separate cohort of mice treated identically using a 20-fold larger dose of MTX.

The present disclosure is not to be limited in scope by the specific embodiments disclosed in the examples which are intended as illustrations of a number of aspects of the disclosure and any embodiments which are functionally equivalent are within the scope of this invention. Indeed, various modifications of the disclosure in addition to those shown and described herein will become apparent to those skilled in the art and are intended to fall within appended claims.

A number of references have been cited, the entire disclosures of which are incorporated herein by reference.

What is claimed is:

1. A method for treating an inflammatory disorder in a patient comprising administering at least four uninterrupted cycles of aminopterin or a pharmaceutically acceptable salt thereof in a therapeutically effective amount, wherein the inflammatory disorder is selected from the group consisting of bronchopulmonary dysplasia, systemic lupus erythematosus (SLE), graft-versus-host-disease (GVHD), polymyositis, rheumatoid arthritis, juvenile rheumatoid arthritis, psoriasis, psoriatic arthritis, atopic dermatitis, dermatitis, multiple sclerosis, inflammatory bowel disease, and canine atopic dermatitis, wherein each uninterrupted cycle has from 1 to 5 aminopterin doses, and wherein a duration between a last dose of one uninterrupted cycle and a first dose of a next uninterrupted cycle does not exceed 21 days.

2. The method for treating an inflammatory disorder in a patient of claim 1 wherein the uninterrupted cycle of aminopterin treatment comprises a plurality of doses of aminopterin.

3. The method for treating an inflammatory disorder in a patient of claim 1 wherein the therapeutically effective amount of aminopterin in each uninterrupted cycle is not greater than 0.07 mg aminopterin per kilogram of patient body weight.

4. The method for treating an inflammatory disorder in a patient of claim 1 wherein the uninterrupted cycle of aminopterin comprises administering aminopterin in a tablet, comprising no more than ten tablets and wherein the tablet contains from about 0.0175 mg to about 7 mg aminopterin.

5. The method for treating an inflammatory disorder in a patient of claim 4 wherein the tablet contains from about 0.0175 mg to about 0.5 mg aminopterin.

6. The method for treating an inflammatory disorder in a patient of claim 5 wherein the tablet contains from about 0.025 to about 0.5 mg aminopterin.

7. A method for inhibiting an enzyme dihydrofolate reductase (DHFR) in vivo, comprising administering an effective amount of aminopterin or a salt thereof, wherein the effective amount of aminopterin is administered in uninterrupted cycles and the dose of aminopterin per uninterrupted cycle is from about 0.0005 to about 0.07 mg per kilogram of body weight, wherein each uninterrupted cycle has from 1 to 5 aminopterin doses, and wherein a duration between a last dose of one uninterrupted cycle and a first dose of a next uninterrupted cycle does not exceed 21 days.

8. The method for inhibiting the enzyme DHFR in vivo of claim 7, wherein the percent inhibition of DHFR is greater than 5%.

9. The method for inhibiting the enzyme DHFR in vivo of claim 7, further comprising treating an inflammatory disorder, wherein the inflammatory disorder is selected from the group consisting of systemic lupus erythematosus (SLE), graft-versus-host-disease (GVHD), polymyositis, rheumatoid arthritis, other forms of arthritis, psoriasis, atopic dermatitis, multiple sclerosis, Crohn's Disease, inflammatory bowel disease, and combinations thereof.

10. A method for treating canine atopic dermatitis and bronchopulmonary dysplasia, comprising administering at least four uninterrupted cycles of an effective amount of aminopterin or methotrexate, or a pharmaceutically acceptable salt thereof, wherein each uninterrupted cycle has from 1 to 5 aminopterin doses, and wherein a duration between a last dose of one uninterrupted cycle and a first dose of a next uninterrupted cycle does not exceed 21 days.

11. The method for treating canine atopic dermatitis and bronchopulmonary dysplasia of claim 10 wherein the drug is aminopterin.

* * * * *

UNITED STATES PATENT AND TRADEMARK OFFICE
CERTIFICATE OF CORRECTION

PATENT NO. : 8,129,383 B2
APPLICATION NO. : 11/928890
DATED : March 6, 2012
INVENTOR(S) : John Zebala et al.

Page 1 of 1

It is certified that error appears in the above-identified patent and that said Letters Patent is hereby corrected as shown below:

In the claims column 38, line 25, in Claim 10, delete the word "aminopterin."

Signed and Sealed this
Tenth Day of December, 2013

Margaret A. Focarino
*Commissioner for Patents of the United States Patent and Trademark Office*